US012796936B2

(12) United States Patent
Liberman

(10) Patent No.: US 12,796,936 B2
(45) Date of Patent: Nov. 17, 2026

(54) SYNCHRONIZED THERMAL-OPTICAL IMAGING SYSTEM WITH IN-FIELD RADIOMETRIC CALIBRATION FOR DETECTION OF SUB-CLINICAL INFLAMMATORY SKIN CONDITIONS AND PERSONALIZED ANTI-AGING

(71) Applicant: Membrane Recovery Ltd, Neve Ziv (IL)

(72) Inventor: Boris Liberman, Neve Ziv (IL)

(73) Assignee: MEMBRANE RECOVERY LTD, Neve Ziv (IL)

( * ) Notice: Subject to any disclaimer, the term of this patent is extended or adjusted under 35 U.S.C. 154(b) by 0 days.

(21) Appl. No.: 19/537,354

(22) Filed: Feb. 11, 2026

(65) Prior Publication Data

US 2026/0324980 A1 Oct. 22, 2026

(51) Int. Cl.
*A61B 5/00* (2006.01)

(52) U.S. Cl.
CPC .......... *A61B 5/0077* (2013.01); *A61B 5/0059* (2013.01); *A61B 5/445* (2013.01)

(58) Field of Classification Search
None
See application file for complete search history.

(56) References Cited

U.S. PATENT DOCUMENTS

2007/0237374 A1* 10/2007 Nikiforos ............. A61B 5/0059 382/128
2011/0230942 A1* 9/2011 Herman ................. A61B 5/015 607/96
2013/0116573 A1* 5/2013 Herman ................. A61B 5/444 600/474
2015/0374277 A1* 12/2015 Patwardhan ........... A61B 5/445 600/476

(Continued)

OTHER PUBLICATIONS

Jarang "Multispectral SWIR imaging for equitable pigmentation-insensitive assessment of inflammatory acne in darkly pigmented skin" published by SPIE Digital Library on Mar. 19, 2025, pp. 1-7 (Year: 2025).*

*Primary Examiner* — Jason M Sims
*Assistant Examiner* — Matthew Eric Ogles
(74) *Attorney, Agent, or Firm* — Fresh IP PLC; Clifford D. Hyra; Aubrey Y. Chen

(57) ABSTRACT

A consumer, at-home cosmetic skin analysis system and method are disclosed. During a scan session, the system acquires synchronized long-wave infrared (LWIR) thermal image data and visible-light image data of a user's skin, optionally including a calibration artifact within the field of view. The system perform radiometric calibration, registers and analyzes the synchronized image data to generate one or more outputs indicative of early skin changes associated with acne-related inflammation, redness (erythema), and/or pigmentation, including changes that may occur before such conditions are clearly visible under normal viewing condi- (Continued)

tions. Specifically disclosed is a system that stores data from multiple scan sessions and performs longitudinal trend analysis to identify persistent or increasing patterns and to provide an early cosmetic-purpose alert, thereby enabling the user to take cosmetic-care steps to reduce subsequent visible acne, redness, or pigmentation. The disclosed system is not medical diagnostic equipment.

26 Claims, 5 Drawing Sheets

(56) References Cited

U.S. PATENT DOCUMENTS

2019/0183350 A1* 6/2019 Bonmarin .............. A61B 5/445
2021/0295517 A1* 9/2021 Parrish .................. G01J 5/0846
2024/0252101 A1* 8/2024 Magal .................... A61B 5/443

* cited by examiner

SYNCHRONIZED THERMAL-OPTICAL IMAGING SYSTEM WITH IN-FIELD RADIOMETRIC CALIBRATION FOR DETECTION OF SUB-CLINICAL INFLAMMATORY SKIN CONDITIONS AND PERSONALIZED ANTI-AGING

FIELD

The present disclosure relates generally to consumer skin imaging and cosmetic skin analysis. In particular, the present disclosure relates to imaging-based systems and methods for assessing facial skin characteristics using one or more of thermal infrared sensing, visible-light imaging, and multispectral illumination, and for generating cosmetic-purpose skin assessment outputs, anti-aging scoring, and personalized skincare optimization recommendations.

BACKGROUND

Systems and methods for skin assessment have been proposed in both consumer and clinical contexts using controlled illumination and image analysis of facial skin.

Such systems may be configured to evaluate visible characteristics of skin condition, including texture and coloration, using visible-spectrum imaging and related reflectance processing.

Various approaches have been described using illumination sources that span portions of the visible spectrum and, in some cases, near-infrared (NIR) and/or near-ultraviolet (near-UV) ranges, with assessments derived from red-green-blue (RGB) imagery and/or diffuse reflectance analysis.

For example, WO2010093503A2 ("Skin analysis methods") describes skin-care devices and methods that illuminate skin and generate skin-condition assessments based at least in part on RGB and/or diffuse reflectance analysis.

Other approaches focus on reflectance imaging to evaluate pigmentation-related characteristics, and note the use of spectral information to evaluate skin constituents such as melanin and hemoglobin.

By way of example, U.S. Pat. No. 8,498,460B2 ("Reflectance imaging and analysis for evaluating tissue pigmentation") discusses computer-aided skin analysis and the use of spectral information to evaluate pigmentation-related constituents.

Multispectral and colorimetric imaging systems have also been described in which a known reference target (e.g., a "white target") occupies a portion of a scene to support calibration and reduce variability attributable to illumination and camera response.

For example, US20110176029A1 ("Multispectral and Colorimetric Imaging System") describes multispectral/colorimetric imaging architectures and the use of a known white target to simplify calibration and compensate for illumination/camera variability.

Beyond patent literature, publications have described estimation of melanin- and hemoglobin-related parameters and/or oxygenation from spectral or RGB-derived reflectance.

For example, Nishidate et al. (Sensors, 2013) reports estimation of melanin and hemoglobin (and oxygen saturation) based on reconstructed spectral reflectance information from RGB imagery, and Kikuchi et al. (Skin Research and Technology, 2013) describes spectral imaging for facial chromophore mapping including melanin and oxy-/deoxy-hemoglobin.

Smartphone-enabled and portable multispectral imaging systems have also been investigated for skin applications and may incorporate calibration aids to improve reproducibility of spectral signatures.

For example, Kim et al. (2016) describes a smartphone-attached multispectral imaging system for management of skin lesions and discusses calibration using a white target, and He et al. (2021) describes smartphone-enabled remote multispectral photoplethysmography methods for monitoring oxyhemoglobin and deoxyhemoglobin-related signals in skin.

Multi-modal devices combining spectral imaging and thermal measurements have been proposed in other contexts.

For example, Rubins et al. (Biosensors, 2019) describes a compact hybrid device involving multi-wavelength illumination and a thermal camera for monitoring skin oxygen saturation and temperature distribution.

In addition, artificial intelligence (AI) and machine learning (ML) have been used with visible-light facial images to classify facial skin characteristics and generate personalized recommendations.

By way of example, U.S. Pat. No. 10,990,858 B2 ("Machine-Implemented Facial Health and Beauty Assistant") describes accepting an image depicting a user's facial skin, applying machine learning models to classify facial skin characteristics, and providing a regimen recommendation based on the classified facial skin characteristics.

The same reference also describes use of a mirror device circumscribed by a ring illuminator to define a temporally consistent illumination standard for acquiring facial images.

Other approaches have proposed longitudinal skin tracking using visible-light cameras operating in uncontrolled environments, including vehicle interiors.

By way of example, U.S. Pat. No. 11,589,803 B2 ("Methods and Systems for Improving Human Facial Skin Conditions by Leveraging Vehicle Cameras and Skin Data AI Analytics") describes facial skin analysis using vehicle cameras, comparing facial images across time periods to determine skin conditions, and transmitting treatment recommendations to a seat occupant, including through a data center and AI analytics.

Further, AI-assisted skincare personalization has been proposed in which a computing system determines features from face data (including facial structure, skin tone, and facial movement) and classifies a subject into a predicted "skin ageotype" used for generating a personalized skincare recommendation.

By way of example, US 2024/0298960 A1 ("Predicting Aging Treatment Outcomes Based on a Skin Ageotype") describes receiving data depicting a face, determining features, providing features to an ageotype classifier to generate a predicted ageotype, and generating a personalized skincare recommendation based on at least the predicted ageotype.

Such approaches may support AI-driven anti-aging guidance by predicting likely clinical signs of aging and recommending skincare interventions accordingly.

Infrared thermography-based systems for body temperature measurement and tissue monitoring have been described in several contexts. US 2021/0393139 A1 (Manneschi et al.) describes an archway-based fever screening system using infrared and visible spectrum cameras with dual thermal reference targets for real-time gain and offset calibration to correct infrared sensor drift. U.S. Pat. No. 11,625,828 B2 (Parrish et al., Seek Thermal) describes a fever detection system employing a temperature-controlled calibration source within the camera field of view, combined with facial recognition to locate regions of interest for real-time thermography calibration. US 2024/0324948 A1 (Donevant et al.) describes using affordable infrared thermography with AI to detect sub-skin tissue damage through temperature deviations associated with microvascular blood flow alterations. While these references demonstrate calibration approaches for infrared imaging and AI-assisted thermal analysis for medical screening, they do not address synchronized thermal-optical imaging with in-field radiometric calibration for longitudinal consumer skin analysis, chromophore-resolved spectral imaging, or predictive detection of sub-clinical inflammatory changes prior to visible manifestation.

Thermal imaging systems combining thermal cameras with visible cameras and in-field calibration sources have also been proposed for fever screening, and image calibration methods using controlled-distance devices have been proposed for skin condition monitoring. By way of example, US 2021/0295517 A1 ("Cost Effective, Mass Producible System for Rapid Detection of Fever Conditions Based on Thermal Imaging") describes a system with a temperature-controlled calibration source within the camera field of view and facial pattern recognition for real-time thermography calibration, and US 2024/0144552 A1 ("Image Reconstruction Device . . . for Monitoring a Medical or Cosmetic Skin Condition") describes an image reconstruction device using a calibration tube for controlled-distance imaging and multi-layer image fusion for longitudinal skin monitoring.

Given the above approaches, several technical limitations remain for practical, consumer-grade early detection and prognosis of inflammatory events and for reliable longitudinal monitoring under variable home conditions.

In particular, many systems provide single-session assessments rather than robust longitudinal tracking under uncontrolled home lighting and rely on generic or indirect color metrics that can be confounded by subject pigmentation and illumination variability.

Many systems do not consistently fuse thermal information with chromophore-resolved vascular/pigmentation information within the same registered region of interest and are not structured to detect temporally ordered physiological patterns that precede visible manifestations of inflammatory lesions.

Numerous mobile applications utilize AI to analyze skin health using standard smartphone cameras, but such camera-only approaches operate in the visible spectrum and are limited to detecting existing, surface-level symptoms.

Accordingly, such approaches may not detect sub-dermal inflammation that has not yet altered the skin's visible appearance.

Infrared thermography has been used to detect inflammation, but miniaturized consumer thermal imaging modules can exhibit drift (e.g., uncooled microbolometer drift) that degrades absolute temperature accuracy and can mask subtle thermal signatures associated with early inflammatory changes.

Additionally, thermal-only approaches can produce false positives due to physiological fluctuations such as blushing or exercise when thermal data is evaluated without sufficient context.

There is also a need for reliable consumer tools that support objective monitoring of redness (erythema) trends associated with irritation or intolerance to cosmetic products, including multi-day changes that may be subtle under normal viewing conditions.

Existing camera-only approaches are sensitive to ambient lighting, white balance, and day-to-day capture variability, and therefore can fail to reliably detect small multi-day changes in redness intensity.

Facial hyperpigmentation disorders, including solar lentigines, melasma, and post-inflammatory hyperpigmentation (PIH), may benefit from early detection of sub-clinical inflammation to enable preventive intervention, but existing dermatological imaging systems may lack synchronized visible-light and thermal measurement in a repeatable home environment and may lack longitudinal trend analysis with sufficient repeatability.

Acne vulgaris is a chronic inflammatory condition affecting the pilosebaceous unit, and lesion development may include a sub-surface inflammatory phase that can last on the order of about 24 to 48 hours before visible signs appear.

Infrared thermography has been demonstrated to correlate with acne severity, with studies showing temperature differences of approximately 2-4° C. between severe acne zones and post-treatment skin (see Padilla-Medina et al., J Biomed Opt., 2014).

As a result, consumer interventions are frequently reactive rather than preventive, and there remains a need for improved systems and methods capable of detecting the prodromal phase of inflammation to enable earlier cosmetic-purpose intervention.

Accordingly, there remains a need for improved consumer systems and methods that can robustly acquire and normalize multi-spectral visible-light data, acquire and stabilize thermal infrared data, and support repeatable longitudinal analysis across scan sessions performed under variable environmental conditions.

There also remains a need for consumer skincare systems that can provide personalized optimization outputs, including anti-aging-related optimization features, based on objective longitudinal measurements rather than single-session appearance alone.

SUMMARY

The present disclosure, in embodiments, provides consumer, at-home cosmetic systems, devices, and methods for predictive and longitudinal skin analysis using synchronized long-wave infrared (LWIR) thermography and visible-light imaging.

In certain embodiments, the disclosed systems and methods are configured to provide early, cosmetic-purpose indications of skin changes associated with acne-related inflammation, redness (erythema), and pigmentation, including providing an indication of a developing inflammatory event before it becomes clearly visible under normal viewing conditions.

In certain embodiments, a system includes a thermal infrared imaging module configured to acquire thermal image data and a visible-light camera configured to acquire visible-light image data of a subject during a scan session.

In certain embodiments, the thermal infrared imaging module is configured for long-wave infrared sensing in an approximately 8-14 micrometer spectral band using an uncooled microbolometer array.

In certain embodiments, the visible-light camera comprises a red-green-blue (RGB) camera of a host device and is configured to capture visible-spectrum image data usable for erythema-related metrics, pigmentation-related metrics, anatomical landmark detection, and user-facing visualization.

In certain embodiments, the systems and methods further use a calibration artifact, also referred to herein as a standard device (SD), positioned on or near the subject and within a field of view of the thermal infrared imaging module and the visible-light camera.

In certain embodiments, the SD includes at least a first thermal reference region having a first emissivity characteristic and a second thermal reference region having a second emissivity characteristic different from the first emissivity characteristic, thereby providing an emissivity-diverse thermal reference.

In certain embodiments, the SD further includes an optical temperature indicator (e.g., a thermochromic liquid-crystal temperature indicator) configured to provide an optical readout of local skin temperature as observed by the visible-light camera, and visible-light reference features (e.g., color reference patches) configured to support visible-light normalization.

In certain embodiments, the system performs in-field thermal calibration by using thermal measurements of the SD thermal reference regions together with an absolute temperature value derived from the optical temperature indicator to determine one or more calibration parameters for the thermal infrared imaging module (e.g., gain and offset parameters) and to generate a calibrated facial temperature map.

In certain embodiments, the calibration artifact comprises a plurality of independently controlled thermal reference surfaces whose temperatures are automatically adjusted (e.g., responsive to a user-selected skin region or a detected region of interest) so that the reference surfaces bracket an expected temperature range of the selected skin region, thereby improving calibration accuracy across different facial zones and skin conditions.

In certain embodiments, visible-light color correction and/or white-balance correction is performed using the SD visible-light reference features so that erythema and pigmentation metrics are more repeatable across scan sessions acquired under different ambient lighting.

In certain embodiments, thermal image data is registered to visible-light image data to generate a registered multi-modal dataset in which thermal features and optical features correspond to the same anatomical locations.

In certain embodiments, registration is performed using SD features detectable in both the thermal domain and the visible domain to compute a geometric transformation (e.g., a homography) and to warp the calibrated thermal temperature map into the visible-light coordinate system.

In certain embodiments, the registered multi-modal dataset is analyzed to identify a candidate skin region that exhibits a thermal anomaly indicative of sub-clinical inflammation while lacking a corresponding visible inflammatory signature in the visible-light image data, thereby identifying a pre-lesion candidate region.

In certain embodiments, longitudinal tracking across sequential scan sessions is used to evaluate persistence of the candidate region over time and to improve robustness against transient thermal variations.

In certain embodiments, the system generates one or more outputs comprising at least a lesion risk score and an associated confidence value indicative of a predicted future visible manifestation of an inflammatory lesion in the candidate region.

In addition to lesion prediction, in certain embodiments the disclosed systems and methods monitor facial skin redness (erythema) indicative of irritation or intolerance to cosmetic products, wherein a redness trend is determined from scan sessions acquired across multiple days and is reported before the subject can readily perceive the redness by normal view.

In certain embodiments, the redness trend is determined using one or more redness metrics derived from visible-light image data, including at least one of a red-green index, normalized red reflectance, and/or hue-saturation-based metrics.

In addition to lesion prediction and erythema monitoring, in certain embodiments the disclosed systems and methods characterize and track pigmentation-related conditions, including post-inflammatory hyperpigmentation (PIH), melasma, and solar lentigines, by tracking a thermal-erythema-pigmentation cascade across sequential scan sessions.

In certain embodiments, a melanin reference region on the SD provides a colorimetric reference for normalizing pigmentation metrics derived from visible-light image data across sessions.

In certain embodiments, the system further comprises a multi-spectral active illumination module configured to sequentially illuminate the subject's skin with a plurality of narrow-band wavelength bands including at least blue, green, and red, and optionally including ultraviolet (UV) and/or near-infrared (NIR).

In certain embodiments, the system acquires a multi-spectral visible-light dataset by sequentially activating narrow-band emitters and capturing at least one frame per wavelength band, and computes chromophore-related outputs including at least one of a melanin-related output, an oxyhemoglobin-related output, and a deoxyhemoglobin-related output.

In certain embodiments, at least one UV-excited fluorescence frame is acquired and processed to compute a porphyrin fluorescence index usable as an acne-relevant follicular activity indicator.

In certain embodiments, artificial intelligence (AI) and/or machine learning (ML) models are applied to one or more of calibrated thermal features, visible-light features, chromophore-resolved features, fluorescence features, and longitudinal features derived from sequential scan sessions to generate a personalized cosmetic-purpose output.

In certain embodiments, the personalized output includes AI-driven anti-aging and personalized optimization features, including one or more of: an individualized skin score, a longitudinal skin trend score, a personalized skincare optimization recommendation, and/or an anti-aging regimen adjustment recommendation based on measured longitudinal response patterns.

In certain embodiments, a skin analysis system comprises a thermal camera configured to capture at least one thermal image of skin of a user, the at least one thermal image comprising thermal image data, a visible-light camera configured to capture at least one visible-light image of the skin of the user, the at least one visible-light image comprising visible-light image data, a calibration device comprising a plurality of thermal reference regions and a plurality of visible-light reference features, and at least one processor operably coupled to the thermal camera and the visible-light camera, wherein the thermal camera and the visible-light camera are configured to acquire, during a same data-acquisition event, (A) the at least one thermal image and (B) the at least one visible-light image, while the calibration device is within a field of view of the thermal camera and within a field of view of the visible-light camera, wherein the skin of the user has not been cooled immediately prior to the same data-acquisition event, and wherein the at least one processor is operatively connected to at least one non-transitory, computer readable medium having instructions stored thereon that, when executed by a computing device, cause the computing device to perform operations, the operations comprising: performing radiometric calibration of the thermal image data using the plurality of thermal reference regions to obtain calibrated thermal image data, registering at least a portion of the calibrated thermal image data with at least a portion of the visible-light image data using the plurality of visible-light reference features and the plurality of thermal reference regions to associate thermal values and visible-light values with corresponding skin locations, determining, based on the registered calibrated thermal image data and the registered visible-light image data, one or more candidate skin regions exhibiting localized thermal elevation exceeding a thermal threshold while a corresponding visible-light metric remains below a visible inflammatory threshold, thereby identifying a developing condition prior to clear visibility under normal viewing conditions, and generating, based on the determining the one or more candidate skin regions, an output indicative of a predicted future visible manifestation for the one or more candidate skin regions, wherein the predicted future visible manifestation is of at least one acne-related condition selected from the group consisting of: inflammation, redness, erythema, or pigmentation, within a future time window, wherein the thermal camera is configured to sense radiation in a spectral band of 8-14 micrometers.

In certain embodiments, a method for cosmetic skin analysis comprises positioning a calibration device comprising a plurality of thermal reference features and a plurality of visible-light reference features within a field of view of a thermal camera and within a field of view of a visible-light camera, capturing, during a same data-acquisition event while the calibration device remains within the field of view of the thermal camera and within the field of view of the visible-light camera, (A) thermal image data of skin of a user using the thermal camera and (B) visible-light image data of the skin using the visible-light camera, wherein the skin of the user has not been cooled immediately prior to the same data-acquisition event, performing radiometric calibration of the thermal image data using the at least one thermal reference feature to obtain calibrated thermal image data, registering at least a portion of the calibrated thermal image data with at least a portion of the visible-light image data using the plurality of visible-light reference features and the plurality of thermal reference features to associate thermal values and visible-light values with corresponding skin locations, determining, based on the registered calibrated thermal image data and the registered visible-light image data, one or more candidate skin regions exhibiting a localized thermal elevation exceeding a thermal threshold while a corresponding visible-light metric remains below a visible inflammatory threshold, thereby identifying a developing condition prior to clear visibility under normal viewing conditions, and generating, based on the determining the one or more candidate skin regions, an output indicative of a predicted future visible manifestation for the one or more candidate skin regions, wherein the predicted future visible manifestation is of at least one acne-related condition selected from the group consisting of: inflammation, redness, erythema, or pigmentation, within a future time window, wherein the thermal camera is configured to sense radiation in a spectral band of 8-14 micrometers.

The disclosed systems and methods are intended for consumer cosmetic-purpose monitoring and guidance and are not medical diagnostic equipment.

BRIEF DESCRIPTION OF THE DRAWINGS

The accompanying drawings illustrate example embodiments of the invention and are incorporated herein to provide a further understanding of the invention. The drawings are not intended to limit the invention to the particular embodiments disclosed.

DETAILED DESCRIPTION

Figure 1A:
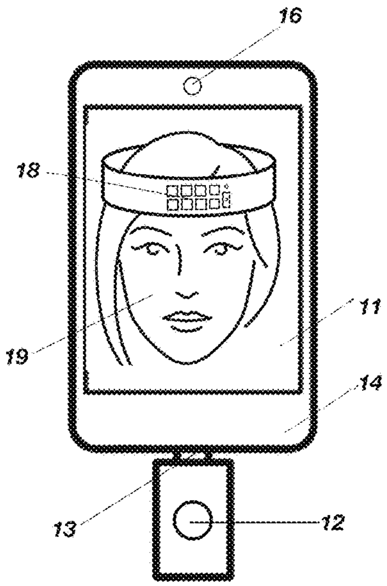
FIGS. 1A and 1B are schematic diagrams illustrating example system configurations for acquiring thermal image data and visible-light image data of a subject and providing such data for calibration, registration, and analysis.

In the following description, references are made to the accompanying drawings that form a part hereof and that illustrate example embodiments of the invention. The embodiments are provided for purposes of illustration and not limitation, and features described in connection with one embodiment may be combined with, omitted from, or substituted into other embodiments unless the context requires otherwise. For example, the "host device" may comprise any suitable computing apparatus configured to receive thermal and visible-light image data, execute one or more calibration, registration, and analysis operations, and provide user-facing output, including a smartphone, tablet, laptop computer, desktop computer, embedded processor, or remote computing resource, and the described data processing may be performed locally, remotely, or in a distributed manner

Definitions

As used in this disclosure, the following terms have the meanings set forth below, and these definitions apply to the claims unless the context clearly indicates otherwise.

Unless expressly stated otherwise, "predetermined" means stored in memory prior to evaluation of a given scan session (e.g., factory-set, user-set, clinician-set, or learned and stored from prior sessions).

Unless expressly stated otherwise, thresholds may be implemented as fixed thresholds, zone-specific thresholds, and/or subject-specific thresholds derived from historical scan data for the same subject.

Scan session means a data-acquisition event in which at least one thermal image and at least one visible-light image of a subject's skin are captured during the same session while the wearable calibration artifact is within the field of view of the thermal camera and the visible-light camera.

Processor means any electronic hardware component or combination of components capable of executing instructions to perform data processing operations. The term "processor" includes, without limitation:

(a) a general-purpose central processing unit (CPU);
(b) a microprocessor, microcontroller, or system-on-chip (SoC);
(c) a graphics processing unit (GPU);
(d) a digital signal processor (DSP);
(e) an application-specific integrated circuit (ASIC);
(f) a field-programmable gate array (FPGA);
(g) a neural processing unit (NPU) or AI accelerator; or
(h) any combination of the foregoing.

A processor may be implemented as a discrete component, as part of an integrated circuit, or as a processing subsystem of a host device such as a smartphone, tablet, laptop computer, desktop computer, embedded system, or cloud computing resource. A processor operates in conjunction with non-transitory memory storing executable instructions that, when executed by the processor, cause the processor to perform the functions described herein. The term "processor" as used herein denotes structure.

In general, the word "instructions," as used herein, refers to logic embodied in hardware or firmware, or to a collection of software units, possibly having entry and exit points, written in a programming language, such as, but not limited to, Python, R, Rust, Go, SWIFT, Objective-C, Java, JavaScript, Lua, C, C++, or C#. A software unit may be compiled and linked into an executable program, installed in a dynamic link library, or may be written in an interpreted programming language such as, but not limited to, Python, R, Ruby, JavaScript, or Perl. It will be appreciated that software units may be callable from other units or from themselves, and/or may be invoked in response to detected events or interrupts. Software units configured for execution on computing devices by their hardware processor(s) may be provided on a computer readable medium, such as a compact disc, digital video disc, flash drive, magnetic disc, or any other tangible medium, or as a digital download (and may be originally stored in a compressed or installable format that requires installation, decompression or decryption prior to execution). Such software code may be stored, partially or fully, on a memory device of the executing computing device, for execution by the computing device. Software instructions may be embedded in firmware, such as an EPROM. It will be further appreciated that hardware modules may be comprised of connected logic units, such as gates and flip-flops, and/or may be comprised of programmable units, such as programmable gate arrays or processors. Generally, the instructions described herein refer to logical modules that may be combined with other modules or divided into sub-modules despite their physical organization or storage. As used herein, the term "computer" is used in accordance with the full breadth of the term as understood by persons of ordinary skill in the art and includes, without limitation, mainframe computers, servers, desktop computers, laptop computers, embedded computers, tablets, smartphones, handheld computing devices, and the like.

In this disclosure, references are made to users performing certain steps or carrying out certain actions with their client computing devices/platforms. In general, such users and their computing devices are conceptually interchangeable. Therefore, it is to be understood that where an action is shown or described as being performed by a user, in various implementations and/or circumstances the action may be performed entirely by the user's computing device or by the user, using their computing device to a greater or lesser extent (e.g. a user may type out a response or input an action, or may choose from preselected responses or actions generated by the computing device). Similarly, where an action is shown or described as being carried out by a computing device, the action may be performed autonomously by that computing device or with more or less user input, in various circumstances and implementations.

In this disclosure, various implementations of a computer system architecture are possible, including, for instance, thin client (computing device for display and data entry) with fat server (cloud for app software, processing, and database), fat client (app software, processing, and display) with thin server (database), edge-fog-cloud computing, and other possible architectural implementations known in the art.

Configured to means that the processor has been programmed, designed, or arranged with the necessary hardware and/or software to perform the specified function. The phrase "configured to" denotes that the processor possesses the requisite structure, circuitry, and/or stored instructions to accomplish the recited function.

Wearable calibration artifact and standard device (SD-18) mean a wearable device configured to be positioned on the subject's skin during a scan session and comprising (i) visible-light color reference patches and/or a distinct marking forming a geometrical reference feature, (ii) a skin-temperature reference, and (iii) at least one additional thermal reference feature.

Non-wearable standard device (SD-18') means a non-wearable, in-scene calibration artifact configured to be positioned within a field of view of the thermal camera and the visible-light camera during a scan session without being attached to, or in direct contact with, the subject, and comprising (i) visible-light color reference patches and/or a distinct marking forming a geometrical reference feature, (ii) one or more thermal reference regions having respective predetermined temperature setpoints and/or known emissivity characteristics, and (iii) a support and/or temperature control unit configured to maintain the one or more thermal reference regions at the respective predetermined temperature setpoints. Geometrical reference feature means one or more markings, patches, fiducials, shapes, or patterns on the wearable calibration artifact that are detectable in the thermal image and/or the visible-light image and are usable to support image registration.

Skin-temperature reference means a reference configured to provide a temperature corresponding to a local skin temperature of the subject during the scan session, including an optical temperature indicator readable by the visible-light camera and/or an electronic sensor.

Additional thermal reference feature means a thermal reference region having a known emissivity and/or a heating element configured to provide a thermal reference region at a temperature elevated relative to local skin temperature or at a fixed elevated temperature.

Thermal image means image data captured by the thermal camera representing long-wave infrared emission and/or corresponding radiometric values and/or apparent temperature values for pixels.

Thermal calibration parameters mean parameters determined using at least the skin-temperature reference and the additional thermal reference feature to calibrate the thermal image, including radiometric gain and offset parameters in certain embodiments.

Calibrated skin temperature map means thermal image data after applying the thermal calibration parameters to the thermal image to generate a drift-reduced, repeatable temperature representation of the subject's skin.

Local thermal elevation means a temperature contrast for a pixel or region relative to surrounding tissue (e.g., relative to a neighborhood mean or a zone baseline) in the calibrated skin temperature map.

Visible-light image means an image captured by the visible-light camera in the visible spectrum (e.g., RGB), optionally color-normalized using the visible-light color reference patches.

Visible-light metric means a quantitative value or map derived from the visible-light image for a pixel, region, ROI, or anatomical zone, including erythema metrics and pigmentation-related metrics.

Erythema metric means a redness proxy derived from the visible-light image.

Composite erythema index means a redness metric computed as a function (e.g., weighted sum) of two or more erythema metrics, optionally including an indicator selecting a target hue range associated with redness.

Visible inflammatory threshold means a predetermined threshold applied to a visible-light metric that quantifies erythema (including an erythema metric or the composite erythema index), wherein the visible inflammatory threshold defines whether a region exhibits visible inflammation for purposes of candidate classification.

Below a visible inflammatory threshold means that the visible-light metric value corresponding to a candidate region does not exceed the visible inflammatory threshold as evaluated for that scan session (optionally using zone-specific thresholds).

Increasing erythema metric means that an erythema metric (or composite erythema index) increases across a plurality of scan sessions according to a predetermined increase criterion, including at least one of (i) exceeding a minimum delta between successive scan sessions or (ii) exhibiting a positive slope over time computed from the plurality of scan sessions.

Melanin color sample means a color sample on the wearable calibration artifact having a spectral reflectance curve that mimics an absorption spectrum of human eumelanin and usable as a normalization reference.

Normalized melanin index means a pigmentation-related metric computed by referencing observed RGB values of skin pixels to observed RGB values of the melanin color sample to reduce variability caused by ambient illumination changes.

Visible hyperpigmentation threshold means a predetermined threshold applied to the normalized melanin index (or other defined pigmentation metric) to classify whether hyperpigmentation is visible for purposes of determining a pre-pigmentation phase.

Registration means transforming (e.g., warping) the calibrated skin temperature map into a coordinate system of the visible-light image using the geometrical reference feature so that thermal and visible data correspond to the same anatomical locations.

Anatomical zone means a predefined region of skin (e.g., forehead, cheek, chin, dorsal hand zones, joint ROIs) identified from the visible-light image and used for normalization and thresholding.

Zone baseline means one or more baseline values computed per anatomical zone and usable for normalization and/or thresholding, including per-zone summary statistics (e.g., zone mean temperature, zone thermal variance, zone redness baseline) and optionally incorporating the subject's historical baseline for the same zone from prior scan sessions.

Candidate region and region of interest (ROI) mean a pixel group or localized region identified in the registered multi-modal dataset for evaluation by thermal, visible-light, and temporal logic.

Candidate pre-lesion region means a candidate region exhibiting (i) a local thermal elevation in the calibrated skin temperature map and (ii) a corresponding visible-light metric below the visible inflammatory threshold.

Temporal persistence means that a candidate region (or a corresponding zone-level candidate) satisfies a predetermined persistence criterion across multiple scan sessions, including persistence for at least two consecutive scan sessions separated by a predetermined interval.

Future time window means a predetermined prediction horizon following a scan session within which emergence of a visible inflammatory lesion is predicted, including example horizons of about 24-48 hours in certain embodiments.

Lesion risk score means a scalar value representing a predicted likelihood that a visible inflammatory lesion will emerge within the future time window for a candidate region and/or anatomical zone.

Confidence value means a scalar value indicating reliability of the lesion risk score, wherein the confidence value is reduced when scan-quality indicators (including at least one of poor registration, low SD visibility, or calibration inconsistency) exceed predetermined tolerances.

Thermal-erythema-pigmentation cascade means a longitudinal multi-signal pattern across a plurality of scan sessions in which localized thermal elevation is observed as an early signal, an erythema metric increase is observed as a subsequent signal, and pigmentation-related change (including normalized melanin index change) is observed as a later signal for a corresponding skin region.

Distinguishes between (in the context of a pigmentation risk alert) means classifying a skin region into one of at least two categories using predetermined decision criteria derived from thermal elevation, erythema metrics, and/or normalized melanin index behavior across the plurality of scan sessions.

Active inflammatory hyperpigmentation (for purposes of the alert) means a condition classified when pigmentation-related change is accompanied by at least one active inflammation indicator (including elevated thermal elevation and/or elevated erythema metric relative to thresholds).

Stable post-inflammatory hyperpigmentation (for purposes of the alert) means a condition classified when pigmentation-related change is present while active inflammation indicators (thermal elevation and erythema) remain below thresholds for a predetermined stability.

FIG. 1A illustrates an embodiment of a thermal-optical imaging system configured to acquire at least one thermal image and at least one visible-light image of a subject during a scan session. The system comprises, a user interface 11 presents an image of the subject 19 a thermal infrared imaging module 12 coupled to a host device 14 via a connector 13, wherein the host device 14 comprises or is associated with a visible-light camera 16 (e.g., a front-facing RGB camera). During acquisition, the subject skin 19 is imaged while the subject wears a wearable calibration artifact 18, also referred to herein as a standard device (SD). In certain embodiments, the SD 18 is positioned on a repeatable facial landmark region (e.g., the forehead) to improve placement repeatability across sequential scan sessions.

Figure 1B:
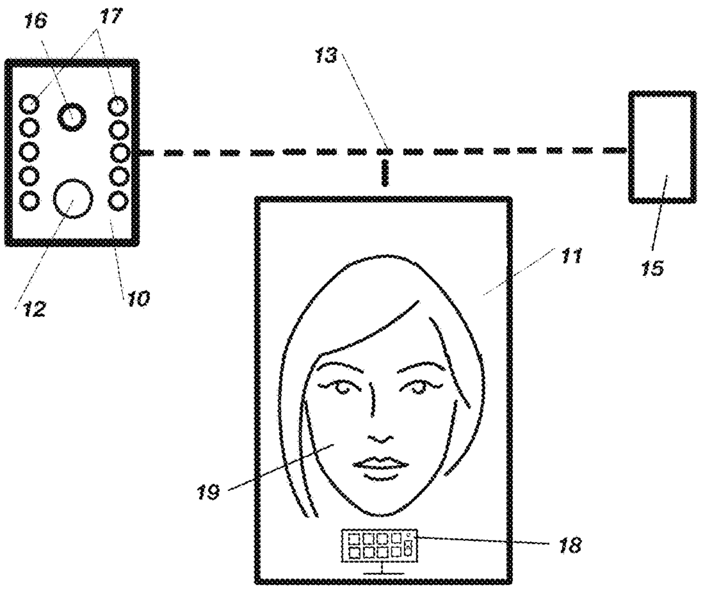

FIG. 1B illustrates an alternative embodiment in which a thermal infrared imaging module 12 and a visible-light RGB camera 16 are arranged as a unitary or co-located sensor assembly. The sensor assembly is communicatively coupled, via a wired interface or a wireless interface, to a processor 15 and an associated user interface 11, wherein the processor 15 comprises one or more of a smartphone, a tablet, a laptop computer, a desktop computer, an embedded processor, or a remote computing resource. In certain embodiments, the user interface 11 presents at least one image of the subject skin 19 and analysis results generated by the processor 15.

In the embodiment of FIG. 1B, a non-wearable calibration artifact 18 is positioned on an independent stand near the subject and within a field of view of the thermal infrared imaging module 12 and the visible-light RGB camera 16, such that the calibration artifact 18 is imaged in-scene without contacting the subject. In certain embodiments, registration of thermal data to visible-light data is performed using facial landmarks detected in the visible-light image and corresponding landmark features in the thermal image, rather than by using a geometric fiducial on the calibration artifact.

Figure 2A:
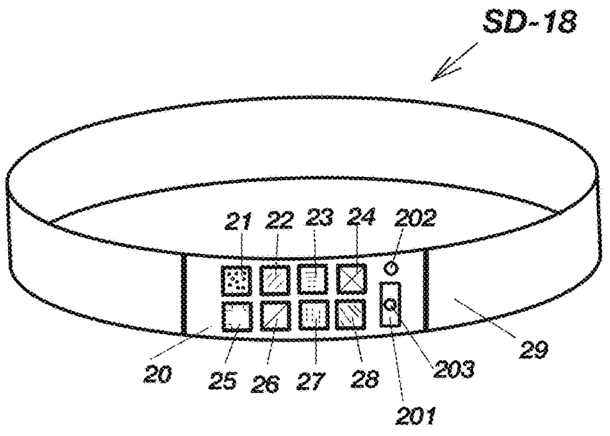
FIGS. 2A and 2B are detailed views of example standard devices (SDs), including a wearable SD-18 (FIG. 2A) and a non-wearable in-scene SD-18' (FIG. 2B), each comprising one or more thermal reference features and one or more visible-light reference features.

FIG. 2A illustrates an embodiment of the wearable standard device SD-18. In certain embodiments, the SD-18 comprises a first thermal reference region 21 having a first emissivity characteristic and a second thermal reference region 22 having a second emissivity characteristic different from the first emissivity characteristic. In certain embodiments, the SD 18 further comprises an optical temperature indicator 23 (e.g., a thermochromic liquid-crystal indicator) configured to provide an optical readout of a local skin temperature, a melanin reference region 24, and a machine-readable code 25 encoding SD-specific parameters. In certain embodiments, the SD 18 further comprises visible-light color reference patches 26, 27, 28 configured to support illuminant estimation, white-balance correction, and repeatable visible-light analysis of erythema and pigmentation across scan sessions.

In operation, the SD-18 is positioned on the subject such that the thermal reference regions 21 and 22 are substantially at a same physical temperature as a local skin region after an equilibration period. The system acquires thermal image data including the regions 21 and 22 and visible-light image data including at least the indicator 23 and the visible-light color reference patches 26-28. In certain embodiments, the processor determines one or more thermal calibration parameters (e.g., gain and offset) for the thermal infrared imaging module using a combination of (i) thermal measurements of the reference regions 21 and 22 and (ii) an absolute temperature value derived from the optical temperature indicator 23, thereby improving absolute temperature repeatability across different environments and scan sessions.

Figure 2B:
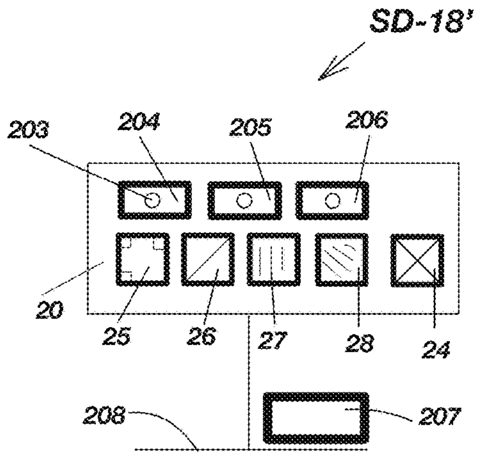

FIG. 2B illustrates an alternative embodiment of a non-wearable standard device SD-18' configured for in-scene thermal and visible-light referencing without contacting the subject. In certain embodiments, the SD-18' is supported by a stand 208 and comprises a plurality of discrete thermal reference regions 204, 205, 206 maintained at respective predetermined temperature setpoints by a temperature control unit 207, wherein the setpoints comprise, by way of example, 30.0° C., 30.3° C., and 30.6° C. In certain embodiments, the SD-18' further comprises visible-light color reference patches 26, 27, 28, a melanin reference region 24, and a machine-readable code 25.

In certain embodiments, the processor uses measured thermal signals from the plurality of thermal reference regions 204-206 and their associated predetermined temperatures to compute thermal calibration parameters (e.g., gain and offset, or a multi-point mapping function) for the thermal infrared imaging module without requiring an on-skin temperature measurement. In certain embodiments, the SD-18' omits emissivity-diverse reference regions and instead provides calibration through the plurality of fixed-temperature reference regions maintained by the temperature control unit 207.

In certain embodiments, the temperature control unit 207 is configured to adaptively adjust predetermined temperature setpoints of a plurality of thermal reference regions 204, 205, 206 of the non-wearable standard device SD-18' based on a user-selected region of interest (ROI). In such embodiments, a user interface 11 presents an image of the subject 19 (e.g., a visible-light image, a thermal image, or a registered overlay), and receives user input identifying an ROI, for example by touch input, pointer input, or selection of a predefined facial zone. The processor 15 determines an estimated temperature of the selected ROI from thermal image data (optionally after local contrast processing and/or landmark-based registration), and computes a set of target reference temperatures for the thermal reference regions 204-206 that bracket or approximate the temperature of the selected ROI. The processor 15 transmits one or more control signals to the temperature control unit 207 to drive the thermal reference regions 204-206 to the computed setpoints, and, after a stabilization criterion is satisfied, acquires a plurality of thermal frames and a plurality of visible-light frames for analysis.

In certain embodiments, the stabilization criterion comprises at least one of: (i) a temperature error of each thermal reference region 204-206 being less than a threshold for a predetermined time interval, (ii) a measured rate of change of each thermal reference region temperature being less than a threshold, or (iii) a controller status output of the temperature control unit 207 indicating thermal steady state. In certain embodiments, the foregoing ROI-driven calibration procedure is repeatable for a plurality of different ROIs selected sequentially by the user, wherein the processor 15 stores an association between each ROI and corresponding calibrated thermal and visible-light data acquired after stabilization.

Thermal Infrared Imaging Module

Figure 3:
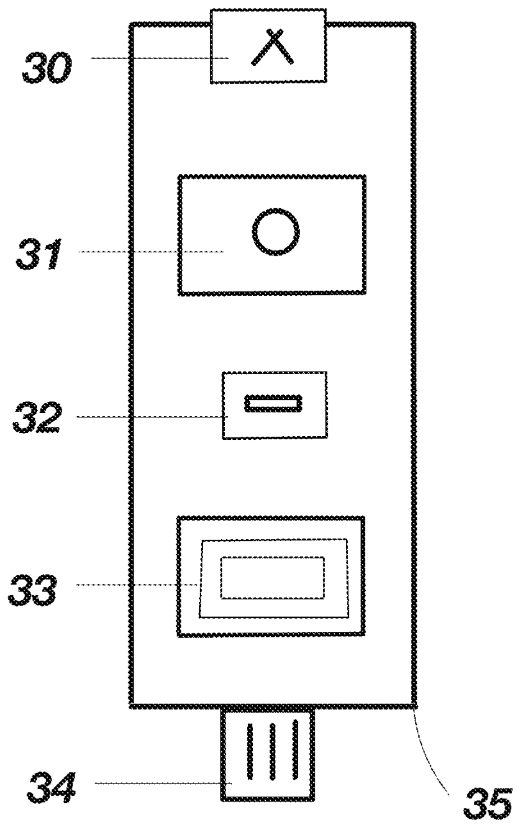
FIG. 3 is a front view of an example thermal infrared imaging module.

FIG. 3 is a front view of a thermal infrared imaging module 12 (FIG. 1A) that may be coupled to a host device 14 (e.g., a smartphone) and configured to acquire thermal image data of a subject, including radiometric temperature data in certain embodiments. In certain embodiments, the thermal infrared imaging module 12 comprises a housing 35 supporting an optical aperture and/or lens assembly 31, a microbolometer array 33, an internal shutter 30, an on-board temperature sensor 32, and a module connector 34 for electrical and data coupling to the host device 14. One or more of these components may be omitted in some implementations, and the module 12 may further include additional components such as processing circuitry, memory, a filter, a window, shielding, or other mechanical/electrical features appropriate for a given design.

In certain embodiments, the thermal imaging module 12 is implemented as a portable dongle configured for close-range facial imaging and is connectable to the host device 14 through the connector 34 (e.g., USB or Lightning). The connector 34 provides power and high-speed serial data transfer enabling the host device 14 to receive streamed thermal frames and to control module functions, including shutter events and telemetry reporting (e.g., temperature sensor 32 readings). In certain embodiments, the interface utilizes a protocol that supports synchronization between thermal frame streaming and visible-light capture by the RGB camera 16, such as by software timestamping of frames.

The housing 35 encloses and supports the optical, sensing, and electronic components of the thermal infrared imaging module 12 and provides mechanical alignment between the lens assembly 31 and the microbolometer array 33. In certain embodiments, the housing 35 provides thermal isolation and/or structural rigidity to reduce drift due to handling and to preserve repeatability of calibration parameters over time. The lens assembly 31 is configured to receive long-wave infrared radiation from a scene (e.g., a subject skin) and to direct the radiation onto the microbolometer array 33.

As depicted in FIG. 3, the microbolometer array 33 comprises an uncooled infrared focal plane array, fabricated using for example vanadium oxide (VOx) or amorphous silicon (a-Si) technology in certain embodiments. The array 33 is configured to produce raw sensor signals representative of thermal radiation incident on a plurality of pixels by detecting changes in electrical resistance without requiring cryogenic cooling. In certain embodiments, the host device 14 and/or firmware in the thermal imaging module 12 converts the raw sensor signals into apparent temperature values and/or radiometrically calibrated temperatures using calibration coefficients and SD-based in-field verification.

In certain embodiments, the internal shutter 30 actuation may be performed at the start of a scan session, periodically during operation, and/or upon detecting drift, and frames acquired during shutter closure may be excluded from facial analysis.

During a scan session, the thermal infrared imaging module 12 captures a thermal map of long-wave infrared radiation emitted by the subject's facial skin and by the wearable standard device SD-18 (FIG. 1A). This thermal map may serve both (i) pre-lesion detection by identifying localized temperature elevations associated with early inflammatory processes and (ii) radiometric calibration input by providing thermal measurements of the SD-18 emissivity-contrast regions (e.g., Regions 21 and 22 shown in FIG. 2A). In certain embodiments, calibrated absolute temperature output from the module 12 improves repeatability across different environments and supports longitudinal tracking across sequential scan sessions.

Integrated Embodiments

While FIG. 1A depicts a modular system comprising a host device 14 and a separable thermal imaging module 12, embodiments of the invention are not limited to this configuration. In alternative embodiments, the thermal imaging module 12 and visible-light camera 16 are integrated into a single dedicated unitary device, such as a "smart mirror" with embedded thermal and optical sensors, a handheld beauty analysis wand, or a tabletop skin monitoring station. In such integrated embodiments, the "host device" functionality (processing, display, and network connectivity) is embedded within the same housing as the sensor assembly. The wearable calibration artifact SD-18 remains a distinct component worn by the user to provide the necessary in-field radiometric and colorimetric reference for the integrated sensors, ensuring that the same predictive thermal-erythema-pigmentation tracking can be performed regardless of whether the sensors are dongle-based or permanently built into a home appliance.

Array Resolution Specifications

In certain embodiments, the thermal infrared imaging module 12 (FIG. 1A, FIG. 3) comprises an uncooled microbolometer array 33 having a baseline resolution of about 160×120 pixels (19,200 thermal pixels). In certain embodiments, a preferred configuration comprises about 256×192 pixels or 320×240 pixels to improve spatial sampling of small inflammatory hotspots on facial skin. In certain embodiments, the microbolometer pixel pitch is about 12-17 micrometers, enabling compact optics and wafer-level packaging suitable for a mobile accessory form factor.

In certain embodiments, the sensor is configured for the long-wave infrared (LWIR) spectral range spanning about 8-14 micrometers, which captures thermal emission from human skin and objects near room temperature. In certain embodiments, the sensor has a target noise-equivalent temperature difference (NETD) of about 50 millikelvin (mK) at 30° C., and preferably about 40 mK, to distinguish temperature contrasts on the order of 0.2-0.3° C. associated with early inflammatory changes. A NETD of approximately 40-50 mK enables detection of localized thermal elevations on the order of 0.3° C., which corresponds to the magnitude of sub-clinical inflammatory signals reported in dermatological literature for early-stage acne lesions.

The use of thermal imaging for acne assessment has been validated using cameras with thermal resolution of 0.2° C. (see Padilla-Medina et al., J Biomed Opt, 2014), supporting the feasibility of detecting the smaller temperature contrasts (e.g., about 0.3° C.) targeted by the present disclosure for early, sub-clinical detection.

These specifications are compatible with commercially available smartphone-oriented thermal cores adapted for mobile integration."

Optical Design

Conventional handheld thermal imagers are optimized for longer distances (e.g., 0.5-2 meters), whereas certain embodiments of the present thermal infrared imaging module 12 are optimized for close-range facial imaging as shown in FIG. 1A. In certain embodiments, the working distance is about 15-25 centimeters from the sensor aperture to the facial plane, corresponding to typical "selfie" distances when using a host device 14. In certain embodiments, the horizontal field of view is about 40-60 degrees, sufficient to capture the full face width at the specified working distance.

In certain embodiments, the lens focal length is selected to be about 6-9 mm depending on microbolometer sensor dimensions, yielding an effective image scale where each thermal pixel represents about 0.5-1.0 mm on the skin surface at about 20 cm distance. This macro-optimized configuration supports localization of small thermal anomalies that may precede visible lesion emergence. In certain embodiments, the optical configuration is chosen to maintain sufficient sharpness for hotspot localization under small variations in user distance.

Lens Assembly

In certain embodiments, the thermal lens assembly 31 (FIG. 3) is constructed from materials that transmit LWIR radiation, including germanium (Ge), chalcogenide glass, and/or silicon (Si). In certain embodiments, anti-reflection (AR) coatings are applied and optimized for wavelengths in the 8-14 micrometer band to reduce reflection losses and improve thermal sensitivity. In certain embodiments, the optical design is configured to reduce vignetting and geometric distortion across the facial field of view.

In certain embodiments, the lens assembly 31 provides a depth of field of about 2-3 cm to accommodate minor variations in user distance without requiring refocusing. In certain embodiments, the lens assembly 31 is integrated into a compact housing 35 (FIG. 3) consistent with a dongle form factor. In certain embodiments, these optical parameters are selected to support repeatable imaging in uncontrolled home environments.

Internal Shutter

As depicted in FIG. 3, in certain embodiments the thermal imaging module 12 includes an internal shutter 30 comprising a flat, high-emissivity surface (e.g., emissivity at least 0.95). The shutter 30 is configured to intermittently block the optical path to provide a uniform thermal reference scene for non-uniformity correction (NUC) and/or flat-field correction. This mechanism compensates for pixel-to-pixel variations in the microbolometer array 33 and for drift due to self-heating and/or ambient changes.

In certain embodiments, shutter actuation is performed at the start of a scan session, periodically during operation, and/or upon detecting drift. In certain embodiments, frames acquired during shutter closure are excluded from facial analysis. In certain embodiments, shutter-based correction operates as a complement to passive in-field calibration using the wearable standard device SD-18 (FIG. 1A, FIG. 2A).

On-Board Temperature Sensors

As shown in FIG. 3, in certain embodiments the thermal imaging module 12 includes one or more on-board temperature sensors 32 attached to the microbolometer substrate 33 and/or the housing 35. The temperature sensors 32 are configured to measure internal module temperatures indicative of detector package conditions to support real-time drift monitoring and compensation. In certain embodiments, the measured temperature is used to select among stored calibration tables and/or to continuously adjust gain and offset correction coefficients.

In certain embodiments, the measured temperature is further used to schedule shutter-based NUC events and/or to annotate thermal frames with telemetry metadata for downstream calibration checks. In certain embodiments, the thermal imaging module 12 is passive with respect to radiation emission and senses emitted thermal energy from objects in its field of view. This passive sensing supports safe close-range facial imaging during routine scan sessions.

Visible Light RGB Camera

The visible-light camera 16 (FIG. 1A) is configured to capture high-resolution images of the subject skin 19 in the visible spectrum (e.g., about 400-700 nm). In certain embodiments, the RGB images are used for at least: (i) visible redness (erythema) assessment, (ii) anatomical landmark detection and facial zone segmentation, and (iii) providing a reference coordinate frame into which the thermal image is registered for multi-modal fusion. In certain embodiments, the RGB images are further used to detect transient artifacts (e.g., hand-face contact and/or facial expressions) that could generate false thermal indications, thereby improving predictive specificity.

In certain embodiments, the system evaluates ambient illumination using visible reference features on the wearable standard device SD-18 (FIG. 1A, FIG. 2A), including color reference patches (e.g., 26-28). In such embodiments, the color references enable white-balance correction and improved repeatability of redness metrics across scan sessions performed under different lighting environments. In certain embodiments, no additional visible-light hardware beyond the host device's integrated front-facing RGB camera is required.

Image Sensor and Resolution

In certain embodiments, the visible-light camera 16 comprises a front-facing image sensor having a resolution in the range of about 7-12 megapixels or higher. In certain embodiments, a minimum target resolution is about 8 megapixels (e.g., 3264×2448 pixels or equivalent) to provide sufficient spatial detail for pore-scale texture assessment, erythema mapping, and robust facial landmark detection at a typical working distance of about 20 cm. In certain embodiments, the visible sensor has a physical pixel pitch of about 1.2-1.8 micrometers, corresponding to an effective spatial sampling on facial skin of about 20-30 micrometers per pixel at the working distance.

In certain embodiments, this high spatial resolution supports geometric alignment of the visible image with the lower-resolution thermal image from the thermal infrared imaging module 12, including sub-region localization of thermal hotspots within anatomical zones. In certain embodiments, the visible-light data is used to derive skin-surface features (e.g., texture and/or redness indices) that are later fused with thermal features for lesion-risk prediction. In certain embodiments, the visible-light camera 16 provides the primary anatomical reference for downstream zone segmentation and output visualization on the host device 14.

Color Accuracy and Dynamic Range

In certain embodiments, the RGB camera 16 provides color encoding in a standard color space (e.g., sRGB or Adobe RGB) and supports accurate white balance under varied illumination conditions. In certain embodiments, the RGB camera 16 provides a dynamic range of at least about 10 stops (approximately 80 dB) to preserve detail in both bright and shadowed facial regions, improving robustness of redness and texture measurements across facial contours. In certain embodiments, the sensor color response provides sufficient gamut to represent a range of skin tones with reduced clipping in the red-yellow-brown hue region relevant to erythema assessment.

In certain embodiments, the system performs color correction using observed RGB values from SD-18 color reference patches (e.g., neutral gray and skin-tone references on the SD-18, FIG. 2A to reduce session-to-session variability in redness metrics. In certain embodiments, the corrected visible-light image is registered with a calibrated facial temperature map to form a registered multi-modal dataset used for prediction of inflammatory skin lesions and/or longitudinal monitoring of erythema.

Multi-Spectral Active Illumination

In certain embodiments, the system further comprises a multi-spectral active illumination module (17) FIG. 1B, integrated with or rigidly co-located on an optical block (10) that houses the visible-light RGB camera (16) and the thermal infrared imaging module (12), such that controlled illumination is provided from substantially the same viewpoint as the imaging sensors. The multi-spectral active illumination module (17) may improve uniform facial illumination at a close-range working distance and may reduce or avoid shadows that may arise when emitters are located elsewhere on the host device or in the environment.

In certain embodiments, the multi-spectral active illumination module (17) comprises a plurality of narrow-band emitters, such as LEDs and/or laser diodes, each configured to emit at a respective wavelength band including at least blue, green, and red, and optionally including ultraviolet (UV) and near-infrared (NIR). In certain embodiments, the emitters are arranged as an annular ring surrounding the RGB camera optical aperture, and optionally surrounding a combined thermal/RGB aperture, to provide substantially uniform illumination across a facial field of view.

In certain embodiments, the multi-spectral active illumination module (17) further comprises driver circuitry controllable by the processor (15) to independently activate each wavelength band and to control one or more emission parameters including current, duty cycle, and/or activation timing. In certain embodiments, the multi-spectral active illumination module (17) optionally comprises polarizing optics, including a polarizer associated with the emitters and an analyzer associated with the RGB camera lens, to reduce specular reflection and enhance subsurface chromophore contrast in the visible-light imagery.

Multi-Spectral Acquisition

In certain embodiments, the processor (15) is configured to acquire a multi-spectral visible-light dataset by sequentially activating narrow-band emitters of the multi-spectral active illumination module (17) and capturing at least one RGB frame per activated wavelength band. In certain embodiments, the processor controls one or more exposure parameters (e.g., exposure time, gain, and/or white-balance lock) such that exposure is held constant for a given wavelength sequence, and/or is adjusted according to a predetermined per-wavelength calibration table to improve inter-wavelength repeatability.

In one non-limiting example acquisition sequence, (i) the processor (15) enables a first wavelength emitter; (ii) after a short settling interval, the RGB camera (16) captures one or more frames; (iii) the processor stores the captured frame(s) with metadata identifying the wavelength band, exposure settings, and timestamp; and (iv) steps (i)-(iii) are repeated for each remaining wavelength emitter to form a multi-spectral image set. In certain embodiments, synchronization between emitter activation and image capture is performed by a hardware trigger and/or by timestamped software control sufficient to associate each captured frame with the correct illumination wavelength band.

In certain embodiments, the processor performs facial landmark detection on one reference RGB frame in the sequence and applies corresponding registration parameters to the remaining wavelength frames to compensate for minor motion, thereby generating a spatially aligned multi-spectral stack suitable for downstream chromophore mapping and longitudinal trend analysis.

Parallax Effect

In certain embodiments, the thermal infrared imaging module 12 (e.g., a dongle) and the host device's front-facing RGB visible-light camera 16 are physically separated by a fixed baseline distance (e.g., about 12-15 cm between optical centers), as illustrated in FIG. 1A. This separation introduces parallax such that the same facial feature appears at different pixel coordinates in the thermal image and the visible-light image when imaging at close range (e.g., about 20 cm working distance). Accordingly, direct overlay of the thermal and visible-light images without geometric correction can yield mis-registration large enough to mis-localize a small hotspot to an incorrect pore/follicular unit.

In certain embodiments, the relative geometry between the thermal infrared imaging module 12 and the RGB camera 16 is characterized during manufacturing and/or during a calibration procedure, and compensation is performed in software using a geometric transformation. In certain embodiments, the two optical axes point in generally the same direction with an angular deviation of less than about 10 degrees, but parallax remains significant at the close-range working distance used for facial scans. In certain embodiments, the wearable standard device SD-18 (FIG. 1A, FIG. 2A) provides a robust multi-modal reference enabling reliable alignment under real-world conditions where user distance and head pose vary between scan sessions.

Calibration Artifact, Standard Device (SD)

FIG. 2A illustrates an embodiment of the wearable calibration artifact SD-18, also referred to herein as a standard device (SD), implemented as a headband assembly having a front mounting region 20 supported by an elastic fabric band 29. The mounting region 20 carries thermal and visible-light reference areas and optionally a machine-readable identifier, arranged to be captured in at least one RGB image and, where applicable, at least one thermal image during a scan session. In certain embodiments, the SD 18 is positioned on a repeatable facial landmark (e.g., the forehead) to improve repeatability of calibration and multi-modal alignment and geometrical reference feature across scan sessions.

In certain embodiments, the SD-18 includes a first thermal reference region 21 comprising a high-emissivity material (Material A) and a second thermal reference region 22 comprising a low-emissivity material (Material B). In use, regions 21 and 22 are configured to thermally equilibrate to substantially the same local skin temperature when the SD-18 is worn on the subject, while producing different apparent thermal readings due to emissivity contrast, thereby enabling robust in-field drift checking and calibration for the thermal infrared imaging module. In certain embodiments, the SD-18 is detectable in the thermal image and in the RGB image, thereby enabling both calibration and image registration in a portable setting.

In certain embodiments, the SD-18 further comprises a thermochromic liquid-crystal temperature indicator which is a form of optical temperature indicator 23 configured to provide an optical readout of local skin temperature $T_{skin}$ as observed by the RGB camera. In certain embodiments, the RGB camera reads the active color and/or segment state of the temperature indicator 23 to obtain an absolute temperature value that is used together with the dual-emissivity regions 21 and 22 to determine thermal calibration parameters (e.g., microbolometer gain and offset) without relying on nominal skin-temperature assumptions. This additional absolute temperature reference can reduce radiometric uncertainty and simplify per-session calibration by converting calibration into a direct computation anchored to T-skin In certain embodiments, the SD-18 further comprises visible color reference patches including a white-tone patch 26, a gray-tone patch 27, and one or more skin-tone patches 28 to support illuminant estimation and color correction for repeatable erythema assessment.

In certain embodiments, the SD-18 further comprises a designated region 24 configured as a melanin color sample (or "melanin reference patch") having a known spectral reflectance profile representative of human skin melanin. Unlike standard white or gray cards that provide general white-balance correction, the melanin color sample 24 is fabricated to exhibit a spectral reflectance curve that mimics an absorption spectrum of human eumelanin (e.g., higher absorption in blue/green wavelengths and higher reflectance in red/near-infrared wavelengths). In certain embodiments, this sample 24 serves as a stable biological proxy in the field of view, allowing the system to normalize pigmentation metrics (such as the Melanin Index described below) against a constant "melanin standard" rather than relying solely on relative skin measurements which drift with lighting changes.

FIG. 2B illustrates an embodiment of a non-wearable standard device SD-18' configured as an in-scene calibration artifact that is positioned near the subject, within the field of view of the thermal camera and the visible-light camera, without contacting the subject during a scan session.

In certain embodiments, SD-18' is supported by a stand 208 and includes one or more thermal reference regions 204, 205, 206 that are maintained at respective predetermined temperature setpoints by a temperature control unit 207, thereby providing a multi-point thermal reference usable to determine thermal calibration parameters for the thermal imaging module.

In certain embodiments, SD-18' further includes visible-light reference features, including color reference patches 26; 27; 28 and optionally a melanin reference region 24 and/or a machine-readable code 25, installed on front mounting region 20 to support color correction.

Longitudinal Pigmentation Tracking and Thermal Erythema-Pigmentation Cascade

In addition to acne and general erythema, the system is configured to characterize and track facial pigmentation disorders (e.g., PIH, melasma, solar lentigines) by monitoring the "thermal-erythema-pigmentation cascade." This cascade posits that localized sub-clinical inflammation (thermal elevation) typically precedes visible redness (erythema), which in turn triggers melanocyte activation and subsequent hyperpigmentation.

To operationalize this, the system computes a Melanin Index (MI) for facial skin pixels using the registered RGB data, normalized by the observed RGB values of the melanin color sample 24. In one embodiment, the Melanin Index is computed as:

$$MI(x, y) = \frac{\log(1/R_{skin}) - \log(1/R_{sample24})}{\log(1/G_{skin}) - \log(1/G_{sample24})}$$

or a similar reflectance-based metric anchored to the sample 24.

The system then generates a Pigmentation Risk Profile by integrating three synchronized signals over longitudinal scan sessions:

1. Thermal History: Persistent localized elevation ($\Delta T \geq 0.3°$ C.) in a specific ROI across multiple days.
2. Erythema Trend: Rising Red-Green Index (RGI) or redness intensity in the same ROI.
3. Pigmentation Velocity: Rate of change in the normalized Melanin Index (MI) relative to the baseline.

A "high risk" of Post-Inflammatory Hyperpigmentation (PIH) is flagged when an ROI exhibits persistent thermal elevation and increasing erythema even before the Melanin Index shows a visible dark spot. This allows the user to intervene with anti-inflammatory or depigmenting agents during the preventative window (e.g., 24-72 hours post-insult) to interrupt the cascade before permanent pigment deposition occurs.

In certain embodiments, the SD-18 further comprises a machine-readable code 25 (e.g., QR code, barcode, or NFC tag) encoding SD-specific and/or batch-specific parameters, including emissivity values and/or reference color values for the calibration methods described herein.

In certain alternative embodiments, the wearable calibration artifact (SD-18) and non-wearable calibration artifact (SD-18') further comprises an active thin-film resistive heating element (201; 204; 205; 206) positioned thermally isolated from the subject's skin. The heating element (201; 204; 205; 206) is controlled by a temperature feedback controller configured to maintain the heating element at a target temperature setpoint, thereby providing a stable, repeatable thermal reference for in-field radiometric calibration of the microbolometer sensor.

In certain embodiments, the heating element (201; 204; 205; 206) comprises a thin-film resistive heater fabricated from a temperature-stable material such as nichrome or polyimide-based resistive film, with dimensions typically in the range of 10-15 mm in length and 3-5 mm in width.

To enable precise temperature regulation relative to the subject's skin, the SD-18 comprises two temperature sensors coupled to the feedback controller:

1. A skin temperature sensor (202) positioned on a non-heated region of the SD substrate in direct thermal contact with the subject's skin, configured to measure the local skin temperature (T-skin).
2. A heater temperature sensor (203) positioned in thermal contact with the heating element (201, 204; 205; 206), configured to measure the instantaneous temperature of the heater (T-heater). (Applicable for wearable calibration artifact SD-18 and non-wearable calibration artifact SD-18')

In certain embodiments, the temperature feedback controller receives input from both sensors (202, 203) and adjusts the electrical power supplied to the heating element (201) to maintain the heater at a specified temperature setpoint. The controller is powered by a coin-cell battery integrated into or attached to the SD-18 substrate.

"In certain embodiments, of non-wearable calibration artifact SD-18'*a* control unit (207) executes a PID control loop that adjusts the temperatures of thermal reference regions (204, 205, 206) so that their radiometric output values bracket or approximate the radiometric values measured in the facial ROI, thereby improving calibration accuracy by placing the reference points near the temperature range of interest."

In certain embodiments, the temperature feedback controller operates in one of two modes:

Dynamic Mode: The controller continuously reads the local skin temperature from the skin temperature sensor (202) and adjusts the power to the heating element (201) such that the heater temperature sensor (203) maintains a value approximately 0.5° C. above the measured skin temperature (i.e., T-heater=T-skin-sensor+0.5° C.). This dynamic tracking provides a relative thermal reference that effectively "brackets" the physiological temperature range, ensuring robust contrast for detecting small thermal anomalies.

Fixed Mode: The controller maintains the heating element (201) at a constant, absolute temperature setpoint of approximately 35.5° C., independent of the reading from the skin temperature sensor (202). In this mode, the controller uses feedback from the heater temperature sensor (203) to hold the heater at the fixed target. This provides a repeatable upper thermal bracket for calibration and simplifies the workflow by providing an absolute temperature anchor.

In operation, the heating element (201) reaches thermal equilibrium with the subject's skin during an equilibration period of approximately 30-90 seconds before image acquisition begins. The stable thermal reference provided by the heating element (201), in conjunction with the passive thermal reference regions (21, 22) and the optical temperature indicator (23), enables robust two-point or multi-point radiometric calibration of the thermal infrared imaging module without relying on assumptions of nominal skin temperature.

SD-Enabled Scanning

In certain embodiments, a user places the SD-18 on a repeatable anatomical landmark (e.g., the forehead) and allows the SD-18 to reach thermal equilibrium with the local skin surface such that regions 21 and 22 are at substantially the same actual temperature as local skin temperature. The system then acquires synchronized imagery including thermal data covering regions 21 and 22 and RGB data covering at least the temperature indicator 23 and the color reference patches 26-28. The system computes radiometric calibration parameters using the emissivity contrast between regions 21 and 22 together with the absolute T-skin derived from the temperature indicator 23, and computes color correction parameters using observed RGB values of patches 26-28.

Anatomical Placements (Hands and Other Body Sites)

In certain embodiments, the wearable calibration artifact SD-18 is adapted for placement on non-facial skin regions, wristband, adhesive patch, spectacle frame. For example, in one embodiment the SD-18 is configured as a wrist-worn band or a dorsal-hand patch for monitoring hand skin conditions post-inflammatory hyperpigmentation on hands, solar lentigines (age spots).

In such embodiments, the SD-18 is secured to the wrist or dorsal hand surface via an elastic band, adhesive patch, or other suitable attachment mechanism. The system acquires synchronized thermal and visible-light images of the hand in a similar manner to the facial workflow described above, with the thermal imaging module 12 and RGB camera 16 positioned above the hand (e.g., the hand rests palm-down on a table surface, and the imaging system is held or mounted above).

The calibration workflow, radiometric correction, erythema metrics (RGI, HSV, Rednorm), and melanin index computation proceed identically to the facial embodiment. In certain embodiments, region-of-interest (ROI) segmentation is adapted for hand anatomy, including detection and tracking of (i) dorsal hand zones (e.g., phalanges, metacarpal regions), (ii) individual hand joints (wrist, MCP joints 2-5, PIP joints 2-5), and (iii) known photoaging sites such as the dorsal metacarpal area.

In certain embodiments configured for occupational hand monitoring, the system performs daily or weekly scan sessions and generates a longitudinal erythema trend report indicating whether redness and/or thermal elevation are increasing over time in response to occupational exposures (e.g., glove occlusion, wet work, chemical contact). An irritation alert is output when the trend exceeds a threshold, enabling early intervention before chronic dermatitis develops.

In certain embodiments configured for hand photoaging and pigmentation tracking, the system monitors solar lentigines or post-procedural PIH using the melanin color sample 24 as a stable reference, enabling objective quantification of treatment efficacy for topical depigmenting agents, laser therapy, or chemical peels applied to the hands.

Additional Form Factors

In certain embodiments, the SD-18 is implemented as an elastic headband that provides repeatable placement on the forehead. In other embodiments, the SD-18 is implemented in other wearable form factors (e.g., an eyeglass-frame form factor or a cosmetic patch form factor) while retaining at least the dual-emissivity thermal reference regions, the temperature indicator 23, and visible color references usable by the RGB camera. Features from different embodiments may be combined or omitted unless otherwise stated.

Redness Index and Color-Based Inflammation Indicators (Erythema Detection Metrics)

After white-balance correction, the RGB image is analyzed for inflammatory redness (erythema) using one or more quantitative redness metrics computed per pixel and/or aggregated over a region of interest. In certain embodiments, the resulting redness map is not used in isolation for lesion detection, but is integrated with thermal data to improve specificity and reduce false positives.

Pre-Processing (Color-Normalization)

Let $R_c(x, y)$, $G_c(x, y)$, and $B_c(x, y)$ denote the corrected (e.g., white-balanced and/or color-corrected) red, green, and blue channel values at pixel (x, y). In certain embodiments, the correction parameters are derived from the SD-18 or SD-18' color reference patches (e.g., white 26, gray 27, and skin-tone 28) so that redness metrics are comparable across sessions and ambient lighting.

Metric 1: Red-Green Index (RGI)

In one embodiment, the red-green index is computed as:

$$RGI(x, y) = \frac{R_c(x, y) - G_c(x, y)}{R_c(x, y) + G_c(x, y) + \varepsilon}$$

where ε is a small constant to avoid division by zero.

In another embodiment, an alternate RGI is computed as:

$$RGI_2(x, y) = \frac{R_c(x, y)}{G_c(x, y) + \varepsilon}$$

Higher RGI values indicate increased red content relative to green, consistent with erythema.

Metric 2: HSV Hue and Saturation

In one embodiment, the corrected RGB values are converted to HSV (Hue, Saturation, Value) and erythema is characterized using hue and saturation. Define:

$$C_{max} = \max(R_c, G_c, B_c),\ C_{min} = \min(R_c, G_c, B_c),\ \Delta = C_{max} - C_{min}$$

Saturation may be computed as:

$$S(x, y) = \begin{cases} 0, & C_{max} = 0 \\ \dfrac{\Delta}{C_{max}}, & C_{max} > 0 \end{cases}$$

Hue may be computed as:

$$H(x, y) = \begin{cases} 0, & \Delta = 0 \\ 60 \cdot \left(\dfrac{G_c - B_c}{\Delta} \bmod 6\right), & C_{max} = R_c \\ 60 \cdot \left(\dfrac{B_c - R_c}{\Delta} + 2\right), & C_{max} = G_c \\ 60 \cdot \left(\dfrac{R_c - G_c}{\Delta} + 4\right), & C_{max} = B_c \end{cases}$$

In certain embodiments, inflamed skin is characterized by hue values in a red range (e.g., about 0-20 degrees) and elevated saturation relative to surrounding tissue.

Metric 3: Normalized Red Reflectance (REDNORM)

In one embodiment, normalized red reflectance is computed as:

$$Red_{norm}(x, y) = \frac{R_c(x, y)}{R_c(x, y) + G_c(x, y) + B_c(x, y) + \varepsilon}$$

This metric tracks the fraction of total brightness attributable to the red channel.

Per-Pixel Erythema Map

In certain embodiments, a composite erythema index EI(x, y) is computed from two or more of the above metrics to yield a robust redness map:

$$EI(x, y) = w_1 \cdot RGI(x, y) + w_2 \cdot Red_{norm}(x, y) + w_3 \cdot S(x, y) \cdot \mathbb{1}_{H \in [H_{min}, H_{max}]}$$

where $w_1$, $w_2$, $w_3$ are weights and $\mathbb{1}_{H\in}[H_{min}, H_{max}]$ is an indicator selecting a target hue range (e.g., red hues).

In certain embodiments, these metrics are computed per-pixel, yielding a spatially resolved redness map that correlates with inflammation severity and is later fused with thermal features for decision logic.

Multi-Spectral Chromophore Decomposition

In certain embodiments, the processor (15) is configured to compute chromophore-specific distribution maps from a multi-spectral image set acquired under sequential narrow-band illumination, thereby separating pigmentation and vascular contributions in the visible-light signal. In such embodiments, the computation uses in-scene visible reference patches on the standard device (SD-18), including at least a white-tone patch (26), a gray-tone patch (27), and one or more skin-tone patches (28), to normalize inter-session and inter-wavelength variability attributable to illumination and camera response.

(a) Reflectance normalization using SD-18 patches (26)-(28). For each illumination band k corresponding to a selected LED wavelength and each pixel location (x,y) on the subject skin, the processor (15) obtains an intensity value I_k(x,y) from the RGB image captured under that band and obtains one or more reference intensities I_k(26), I_k(27), and I_k(28) measured from the SD-18 or SD-18' patches (26)-(28) in the same frame. In certain embodiments, a normalized reflectance proxy R_k(x,y) is computed as R_k(x,y)=I_k(x,y)/(I_k(26)+ε), where I_k(26) is a per-frame or per-session statistic (e.g., mean or median) of the white-tone patch (26) and ε is a small constant to avoid division by zero, and the gray-tone patch (27) and/or skin-tone patch (28) are optionally used as secondary checks to reject frames with saturation, glare, or improper exposure.

(b) Log transform/optical density. The processor (15) computes an optical-density vector A(x,y) by applying a negative logarithm to the normalized reflectance proxies across bands, A_k(x,y)=−ln(R_k(x,y)), which linearizes a Beer-Lambert-type relationship between measured optical density and chromophore absorption.

(c) Non-negative least squares (NNLS) chromophore unmixing. For each pixel (x,y), the processor (15) models the optical-density vector A(x,y) as a non-negative linear combination of basis spectra associated with at least melanin and hemoglobin, and preferably at least melanin, oxyhemoglobin (HbO2), and deoxyhemoglobin (Hb), to obtain a concentration or index vector C(x,y). In certain embodiments, the processor (15) constructs a basis matrix E whose columns correspond to selected chromophore absorption or effective extinction coefficients evaluated at the illumination wavelengths, and solves C(x,y)=argmin_{C≥0}||A(x,y)−E·C||^2 using a non-negative least squares solver to enforce physically meaningful non-negative chromophore values.

In certain embodiments, the processor (15) stores, accesses, and/or derives wavelength-dependent coefficient values for at least melanin, oxyhemoglobin (HbO2), and deoxyhemoglobin (Hb) for use in the chromophore unmixing described above. In such embodiments, HbO2 and Hb coefficients are stored as molar extinction coefficients (e.g., cm/M), while melanin is stored as an effective absorption coefficient (e.g., cm-1) for melanosomes because melanin is typically modeled via absorption coefficient versus wavelength rather than a true molar extinction coefficient. In certain embodiments, the following table provides representative coefficient values at nominal illumination wavelengths of approximately 365 nm, 473 nm, 532 nm, 659 nm, and 850 nm. For wavelengths not explicitly tabulated (e.g., 365 nm, 473 nm, 659 nm), the processor (15) may compute the coefficient via interpolation between adjacent tabulated wavelengths.

TABLE 5.8.4-1

Example coefficients for chromophore unmixing

| Nominal wavelength (nm) | Melanin melanosome absorption a_mel (cm−1) | HbO2 molar extinction (cm/M) | Hb molar extinction (cm/M) |
|---|---|---|---|
| 365 | 1936.91 | 89160.0 (interp.) | 137436.0 (interp.) |
| 473 | 817.06 | 30866.8 (interp.) | 15179.2 (interp.) |
| 532 | 552.41 | 43876.0 | 40584.0 |
| 659 | 270.80 | 322.6 (interp.) | 3273.38 (interp.) |
| 850 | 116.03 | 1058.0 | 691.32 |

Embodiments of the invention are not limited to the particular coefficient dataset, and other published and/or empirically determined coefficient sets may be used. In certain embodiments, a_mel is computed using a power-law approximation for melanosome absorption as a function of wavelength (e.g., a_mel=K·λ^(−m)), with K and m selected from literature, and is scaled by an estimated melanin fraction during unmixing. In certain embodiments, the HbO2 and Hb molar extinction coefficients are obtained from a published hemoglobin extinction dataset and used directly as HbO2/Hb basis vectors in the NNLS solver.

(d) Map outputs. The resulting chromophore indices are assembled into one or more chromophore distribution maps for display and/or downstream fusion with thermal data, where a melanin-related output and a hemoglobin-related output may be generated to provide physiologically meaningful optical features that are less sensitive to melanin masking than RGB redness metrics alone. In certain embodiments, these maps are computed per ROI and tracked longitudinally across scan sessions to improve robustness of erythema trend monitoring and pigmentation risk profiling.

Chromophore Map Generation

In certain embodiments, after computing per-pixel chromophore indices C_mel(x,y), C_HbO2(x,y), and C_Hb(x,y) via the normalization, logarithmic transform, and NNLS unmixing pipeline described above, the processor (15) generates one or more chromophore distribution maps for visualization, ROI analytics, and longitudinal tracking. In such embodiments, the chromophore distribution maps are spatially registered to the visible-light image coordinate system and are optionally fused with the thermal map (e.g., by facial-landmark registration) to produce a multi-modal diagnostic dataset.

(a) Melanin map. In certain embodiments, the processor (15) generates a melanin map M(x,y) defined as M(x,y)= C_mel(x,y), representing a pigmentation-related signal component attributable to melanin absorption. In certain embodiments, the melanin map is additionally normalized using the SD melanin color sample region (24) to reduce session-to-session variability, for example by scaling M(x,y) by a reference value derived from region (24) consistent with the normalized melanin-index approach described elsewhere in the specification.

(b) Oxyhemoglobin and deoxyhemoglobin maps. In certain embodiments, the processor (15) generates an oxyhemoglobin map O(x,y)=C_HbO2(x,y) and a deoxyhemoglobin map D(x,y)=C_Hb(x,y), representing vascular chromophore components associated with erythema/inflammation and tissue oxygenation status. In certain embodiments, these maps are used as quantitative erythema-related features complementary to, or replacing, RGB-derived erythema metrics (e.g., RGI, normalized red reflectance, HSV-based metrics), because the decomposition reduces melanin masking and improves robustness under varying illumination.

(c) Total hemoglobin map. In certain embodiments, the processor (15) computes a total hemoglobin map H_tot(x,y) as H_tot(x,y)=O(x,y)+D(x,y). This map provides an estimate of relative blood-volume or perfusion-related index in the imaged skin region and may be used to detect increased vascularization or irritation-associated perfusion changes within a selected ROI.

(d) Oxygen saturation map. In certain embodiments, the processor (15) computes a relative oxygen saturation map S_O2(x,y) as S_O2(x,y)=O(x,y)/(O(x,y)+D(x,y)+ε), where ε is a small constant to avoid division by zero. In certain embodiments, S_O2(x,y) is used to characterize whether an erythematous region is predominantly oxygenated capillary dilation consistent with active inflammation or relatively deoxygenated venous pooling or other vascular conditions, and the resulting oxygenation features are used by the AI model as part of multi-modal scoring.

(e) ROI aggregation and longitudinal tracking. In certain embodiments, the processor (15) aggregates the foregoing maps over a user-selected ROI or predefined anatomical zone to compute summary statistics (e.g., mean, median, percentile values, and/or spatial variance) for M(x,y), O(x, y), D(x,y), H_tot(x,y), and S_O2(x,y), and stores the results as longitudinal features across multiple scan sessions. In certain embodiments, the system detects and reports trends consistent with a thermal-erythema-pigmentation cascade by identifying a sequence in which thermal elevation precedes an increase in O(x,y) or H_tot(x,y), followed by a later increase in M(x,y), within the same registered ROI.

Radiometric Calibration and Thermal Signal Processing

This section describes the mathematical basis and implementation of the passive radiometric calibration (FIG. 4, Step 42) that converts raw microbolometer output into an absolute facial temperature map suitable for detecting subclinical inflammation. The calibration leverages the wearable standard device (SD-18, including a high-emissivity region 21 (Material A), a low-emissivity region 22 (Material B), and an additional SD-18 provided reference 23, to reduce drift sensitivity and improve absolute accuracy across users and environments. In certain embodiments, region 23 comprises a thermochromic liquid-crystal temperature indicator that is read by the RGB camera to provide an absolute local skin temperature $T_{skin}$, eliminating reliance on nominal skin-temperature assumptions.

Governing Physics (Planck-Based Radiance)

A thermal imaging module measures radiance (or band-integrated radiance), not temperature directly. In one embodiment, spectral blackbody radiance is modeled by Planck's law:

$$L_{bb}(\lambda, T) = \frac{2hc^2}{\lambda^5} \cdot \frac{1}{\exp\left(\frac{hc}{\lambda kT}\right) - 1}$$

where h is Planck's constant, c is the speed of light, k is Boltzmann's constant, λ is wavelength, and T is absolute temperature. Because the sensor operates over a finite LWIR band (e.g., about 8-14 μm), an equivalent band radiance function may be defined as:

$$\Phi(T) = \int_{\lambda_1}^{\lambda_2} \tau(\lambda) L_{bb}(\lambda, T) d\lambda$$

where τ(λ) represents the combined spectral response of optics and detector (including lens transmission and detector responsivity), and $[\lambda_1, \lambda_2]$ spans the sensor band.

Surface Radiance Model (Emissivity and Reflection)

For a surface region i on the SD (e.g., i∈{21,22}), the radiance incident on the detector may be modeled as:

$$\Phi_i = \varepsilon_i \Phi(T_{skin}) + (1 - \varepsilon_i)\Phi(T_{bg})$$

where $\varepsilon_i$ is the emissivity of region i, T-skin is the physical temperature of the SD region after equilibration on skin, and T-bg is an effective background (reflected) temperature representing the radiance reflected by non-black surfaces. In certain embodiments, T-bg is estimated from at least one of (i) a module on-board temperature sensor, (ii) an internal shutter reference, or (iii) the low-emissivity behavior of region 22.

Calibration Methods Using Emissivity Diverse Regions

In-field calibration is executed automatically during the image acquisition phase (e.g., FIG. 4, Step 41-42) to correct microbolometer drift and generate a calibrated facial temperature map. The system uses the SD 18 as a passive in-scene reference by detecting the emissivity-diverse regions 21 and 22 and reading an absolute local skin temperature.

Step 1—Detection (SD Localization).

The system identifies the SD 18 within the thermal image using the geometric pattern of the high-emissivity region 21 adjacent to the low-emissivity region 22. In certain embodiments, the SD is also detected in the RGB image using its visible features (e.g., color patches and/or the indicator 23) to confirm correct placement and visibility.

Step 2—Measurement (Thermal+RGB Absolute Temperature).

The system computes region statistics from the thermal frame, such as mean raw digital counts (or mean linearized signal values) $D_{21}$ and $D_{22}$ for regions 21 and 22, respectively. The system obtains an absolute temperature estimate T-skin by decoding the visible color/segment state of the thermochromic liquid-crystal indicator 23 in the RGB image, wherein the indicator exhibits a calibrated color response as a function of temperature.

Step 3—Solve Gain/Offset Using 21/22/23.

In certain embodiments, the microbolometer is modeled as an affine radiometric response D=G'Φ+0, where Φ is a band-integrated radiance-like quantity, G' is an effective in-field gain, and O is an offset. The expected band signal for SD region i∈{21,22} is modeled as ($\Phi_1=\varepsilon_i\Phi(T_{skin})+(1-\varepsilon_i)\Phi(T_{bg})$, where $\varepsilon_i$ is emissivity of the SD region and $T_{bg}$ is an effective background/reflected temperature. The gain and offset are then solved as:

$$G' = \frac{D_{21} - D_{22}}{\Phi_{21} - \Phi_{22}},\ O = D_{21} - G'\Phi_{21}$$

where $T_{skin}$ is supplied by the thermochromic indicator 23 (RGB readout), thereby avoiding reliance on nominal skin-temperature assumptions.

Calibration Using Active Heating Element

In embodiments where the SD-18 comprises the active heating element (201), the system performs a two-point radiometric calibration by leveraging the stable temperature differential provided by the heater. The system identifies two thermal reference regions in the thermal image:

Skin Temperature Reference Point

The system derives the first calibration point (T-skin, S-skin) corresponding to the subject's local skin temperature.

Signal Source S-skin: The system extracts the raw thermal signal from Region 21 (the high-emissivity passive reference region), which is in thermal equilibrium with the skin.

Temperature Source T-skin: The system determines the absolute temperature value by optically reading the color of the thermochromic liquid-crystal indicator (Region 23) in the visible-light image.

Heater Temperature Reference Point

The system derives the second calibration point (T-skin, S-skin) corresponding to the active heating element.

Signal Source (S-heater): The system extracts the raw thermal signal from the active heating element (Region 201) in the thermal image.

Temperature Source (T-heater): The system derives the absolute temperature value based on the active operating mode:

In Fixed Mode, the system assigns a pre-defined setpoint value (e.g., T-heater=35.5° C.).

In Dynamic Mode, the system calculates T-heater by adding the designated offset to the measured skin temperature (e.g., T-heater=T-skin+0.5° C.).

Calibration Computation

The processor extracts the mean raw thermal signal values S-skin and S-heaters from the corresponding regions and solves for the calibration parameters, Gain (G) and Offset (O), using the linear radiometric model:

$$G = \frac{S_{heater} - S_{skin}}{T_{heater} - T_{skin}}$$

$$O = S_{skin} - G \cdot T_{skin}$$

These parameters are then applied to the full thermal image to generate the calibrated temperature map:

$$T_{pixel} = \frac{S_{pixel} - O}{G}$$

This method ensures robust calibration even in low-contrast environments where passive materials might differ in temperature by only a small fraction of a degree.

Step 4—Validation (Optional) and Correction Application.

In certain embodiments, the system optionally validates calibration by comparing measured SD behavior (e.g., apparent contrast between 21 and 22) to an expected value encoded in the machine-readable identifier 25, and produces a quality score and/or prompts re-acquisition if out of tolerance. The calibrated parameters (G',O) are applied to all pixels in the facial thermal image to correct sensor drift, ambient effects, and lens/transmission changes prior to downstream analysis.

Thermal Signal Processing Pipeline

Raw data from the microbolometer 33 may contain temporal noise and pixel non-uniformity, and therefore is preprocessed before and/or in conjunction with SD-based calibration. In certain embodiments, the pipeline includes bad-pixel replacement (e.g., interpolating dead pixels identified by a factory map). In certain embodiments, the system performs temporal averaging of multiple frames (e.g., 5-10 frames captured during burst acquisition) to reduce noise prior to extracting SD region statistics $D_{21}$ and $D_{22}$.

In certain embodiments, the system applies non-uniformity correction (NUC) using frames acquired via the internal shutter 30 prior to the scan, and excludes shutter-closure frames from skin analysis. In certain embodiments, the ordering is: (i) NUC and denoising, (ii) SD detection/segmentation, (iii) solve (G',O) using regions 21/22 plus T-skin from region 23, and (iv) apply calibration to the full facial thermal frame.

Absolute Temperature Recovery

Once (G',O) are determined from the SD-18 (regions 21/22) anchored by the RGB-derived absolute T-skin from indicator 23, the calibrated radiometric value for any pixel p is computed as:

$$\Phi_p = \frac{D_p - O}{G'}$$

thereby converting raw sensor output into a drift-corrected radiometric domain. In certain embodiments, the system converts $\Phi_p$ to an absolute temperature $T_p$ using an inverse calibration function $T_p=\Phi^{-1}(\Phi_p)$ derived from factory characterization and/or stored calibration tables.

In certain embodiments, a skin emissivity correction is applied to improve absolute accuracy, and one or more pixels corresponding to SD-18 region 21 (high emissivity) are used as a consistency check against the RGB-derived T-skin rather than as the sole absolute reference. The resulting calibrated absolute facial temperature map is then provided to subsequent processing stages including registration and lesion-risk inference.

Accuracy and Performance

To reliably predict acne lesions, the system targets detection of localized inflammatory hotspots on the order of about 0.3° C. to 0.5° C. The disclosed threshold values (e.g., about 0.3° C.) represent design targets for sub-clinical detection that are below the approximately 2-4° C. temperature differences observed between severe acne zones and healthy skin (see Padilla-Medina et al., J Biomed Opt., 2014), and are selected based on the sensor's noise-equivalent temperature difference (NETD) capability to enable detection of inflammatory changes before they reach visible severity.

Consumer thermal cameras without in-field referencing may exhibit absolute inaccuracies of multiple degrees Celsius, which can mask subtle pre-inflammatory signals. By using the SD-18 with emissivity-diverse regions 21 and 22 plus an RGB-readable thermochromic temperature indicator 23 providing an absolute T-skin anchor, the system can reduce calibration uncertainty and improve robustness across users and environments.

In certain embodiments, the system achieves calibrated absolute temperature accuracy on the order of fractions of a degree Celsius (e.g., about 0.4° C. for example) and relative differential precision on the order of tenths of a degree (e.g., about 0.1° C. for example), enabling reliable detection of early-stage inflammation. In certain embodiments, the calibration approach remains suitable for varied home environments (e.g., cool bathrooms vs. warm bedrooms) because the SD-based method provides an in-scene reference rather than relying solely on uncontrolled ambient conditions.

Image Registration and Multi-Modal Fusion

To fuse thermal and RGB information at the pixel level, the system registers (aligns) the calibrated thermal image produced by the radiometric pipeline to the RGB image coordinate system so that a thermal hotspot corresponds to the same anatomical location in the visible image. This registration enables downstream logic to evaluate a candidate region using both thermal features and visible redness/texture features, as described in the FIG. 4 workflow and FIG. 5 inputs.

Coordinate Mapping

In certain embodiments, each imaging unit (thermal module 12 and RGB camera 16) is modeled using a pinhole camera model with intrinsics and extrinsics, and the mapping between the thermal image plane and the RGB image plane is approximated as a planar projective transform over the facial region of interest. Because the SD-18 is positioned on a relatively stable and locally near-planar region (e.g., forehead) during the scan, a homography is sufficient for close-range alignment in many consumer use cases.

In one embodiment, a pixel $(x_t, y_t)$ in the thermal image is mapped to a pixel $(x_v, y_v)$ in the RGB image by a 3×3 homography matrix H operating on homogeneous coordinates:

$$\begin{bmatrix} x_v \\ y_v \\ 1 \end{bmatrix} \sim H \begin{bmatrix} x_t \\ y_t \\ 1 \end{bmatrix}$$

where ~ indicates equality up to scale. In certain embodiments, lens distortion correction (thermal and/or RGB) is applied before estimating H to reduce systematic error in the warping step.

Fiducial Based Registration Algorithm

The SD-18 provides features that are intentionally detectable in both thermal and visible domains, enabling stable correspondence matching even when the skin lacks strong thermal edges. In the thermal domain, region 21 (high emissivity, at least 0.95) and region 22 (low emissivity of less than 0.15) provide a consistent intensity/temperature pattern whose centroid(s), edges, and/or corners can be used as thermal control points. In the visible domain, corresponding control points may be derived from one or more of: (i) boundaries of the SD, (ii) color patches 26-28, (iii) corners of the machine-readable code 25, and (iv) the thermochromic liquid-crystal temperature indicator 23, whose color/segment state provides a high-contrast, easily segmented visible feature.

Figure 4:
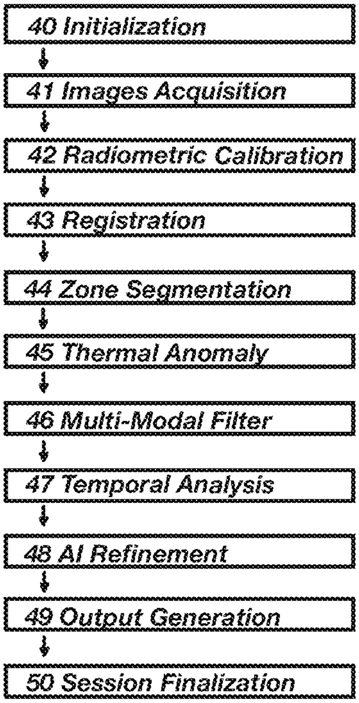
FIG. 4 is a flowchart illustrating an example method for predicting inflammatory skin lesions and/or for longitudinal skin analysis using synchronized thermal and visible-light imaging.

Real-Time Computation Methods (e.g., FIG. 4, Step 43)

In one embodiment, registration proceeds as follows:

- Feature extraction: Detect thermal control points on regions 21-22 in the thermal frame and visible control points on the SD-18 (including optional indicator 23 features) in the RGB frame.
- Matrix estimation: Compute H from the paired point sets using a Direct Linear Transform (DLT), optionally with RANSAC to reject outliers caused by motion blur, partial occlusion, glare, or inaccurate SD-18 segmentation.
- Warping: Warp the thermal image (or the calibrated temperature map) into RGB coordinates using H, and resample to the RGB resolution so that each RGB pixel can be associated with a corresponding thermal value.

In certain embodiments, a refinement step is performed after the initial warp by minimizing a reprojection error objective over SD-18 feature points and/or over facial landmarks detected in RGB, thereby improving sub-region alignment away from the SD-18. In certain embodiments, if the SD-18 is not detected with sufficient confidence in either modality, the system prompts the user to re-acquire the scan before proceeding to lesion prediction.

Anatomical Zone Segmentation and Facial Landmark Detection (e.g., FIG. 4, Step 44)

After the thermal image is aligned into the RGB coordinate space, the system performs facial landmark detection on the RGB image (e.g., using a face mesh model) to identify stable reference landmarks such as eyes, nose, mouth, jawline, and eyebrows. The face is partitioned into predefined regions of interest (ROIs) such as forehead, left/right cheek, and chin, and exclusion masks are generated for non-skin regions (e.g., eyes, lips, nostrils, and hair) to reduce artifacts. Each registered pixel (x, y) is assigned a zone label Z(x, y) so that subsequent thermal anomaly detection can apply zone-specific baselines and thresholds.

Multi-Modal Data Fusion and Creating Fused Tensors

Following completion of registration (e.g., FIG. 4 Step 43), the system generates an aligned multi-modal dataset in which thermal information and visible-spectrum information correspond to the same anatomical locations. In certain embodiments, the aligned dataset is represented as a per-pixel multi-channel tensor F(x,y) defined over facial skin pixels in RGB coordinates.

(A) Fusion Prerequisites—Thermal Stabilization.

In certain embodiments, fusion is performed using a radiometrically calibrated or radiometrically stabilized thermal output produced during the radiometric calibration stage (e.g., FIG. 4 Step 42), such that drift of an uncooled microbolometer sensor is reduced prior to any thermal-to-RGB warping. In certain embodiments, the processor stores one or more thermal calibration quality indicators (e.g., SD-18 visibility, SD-18 segmentation confidence, and/or consistency checks) for later use in confidence weighting and/or reacquisition prompting.

(B) Fusion Prerequisites—Visible Normalization.

In certain embodiments, fusion uses an RGB image that is white-balanced and/or color-corrected using SD-18 visible reference patches (e.g., patches 26-28) to reduce session-to-session variation due to ambient illumination and camera auto white-balance behavior. In certain embodiments, the corrected RGB image provides the reference coordinate frame for subsequent anatomical segmentation and overlay display.

(C) Coordinate Unification by Resampling.

In certain embodiments, the processor warps the calibrated thermal map into RGB coordinates using the computed geometric transform (e.g., a homography H estimated from SD-18 features or other cross-modal correspondences), and resamples the warped thermal map to the RGB pixel grid. In such embodiments, each RGB pixel location (x,y) is associated with a corresponding thermal value and corresponding optical values, thereby enabling pixelwise fusion and localized ROI scoring.

(D) Skin Validity Mask and Artifact Exclusion.

In certain embodiments, the processor generates a binary or soft skin validity mask indicating valid skin pixels and excludes non-skin regions including at least eyes, lips, nostrils, and hair to reduce artifact-driven errors. In certain embodiments, the processor additionally masks pixels affected by saturation, glare/specular reflection, motion blur, and/or SD occlusion, and stores a per-pixel or per-frame quality indicator used to down-weight unreliable channels.

(E) Tensor Definition—Core Channels.

In one embodiment, the fused tensor includes at least the following channels:

Channel 1: Calibrated absolute temperature T(x,y) derived from the radiometrically calibrated thermal image after warping into RGB coordinates.

Channels 2-4: Visible color values R(x,y), G(x,y), B(x,y) (optionally white-balanced using SD color patches).

Channel 5: A local thermal feature such as thermal gradient magnitude $\nabla T(x,y)$ and/or local thermal contrast $\Delta T(x,y)$ relative to a neighborhood baseline.

Channel 6: A redness/erythema feature computed from the RGB data (e.g., a red-green index, normalized red reflectance, and/or other erythema proxy).

(F) Optional Chromophore Channels (Multi-Spectral Reflectance).

In certain embodiments, the system acquires a multi-spectral reflectance image set under sequential narrowband illumination and computes chromophore-related maps that are registered to the RGB coordinate system. In such embodiments, the fused tensor further includes one or more of: a melanin channel M(x,y), an oxyhemoglobin channel O(x,y), a deoxyhemoglobin channel D(x,y), a total hemoglobin channel H_tot(x,y)=O(x,y)+D(x,y), and/or an oxygen saturation channel S_O2(x,y)=O(x,y)/(O(x,y)+D(x,y)+F), where F is a small constant.

(G) Optional Porphyrin Fluorescence Channel (UV-Excited Fluorescence).

In certain embodiments, the system acquires at least one UV-excited fluorescence frame and computes a porphyrin fluorescence index PF(x,y), and registers PF(x,y) to the same RGB coordinate system used for the reflectance and thermal channels. In such embodiments, the fused tensor includes an additional fluorescence channel PF(x,y) usable as an acne-relevant follicular activity indicator and/or as a discriminator during multi-modal filtering and scoring.

(H) Use of the Fused Tensor.

By forming a single fused representation, the system ensures that a candidate thermal hotspot is evaluated together with corresponding visible features and, where available, chromophore-resolved and fluorescence features, which improves discrimination between true developing lesions and benign thermal events. In certain embodiments, scan-quality indicators derived from calibration and registration are used to reduce a confidence output and/or request reacquisition when the fused tensor is unreliable.

Lesion Detection and Prediction Logic

Figure 5:
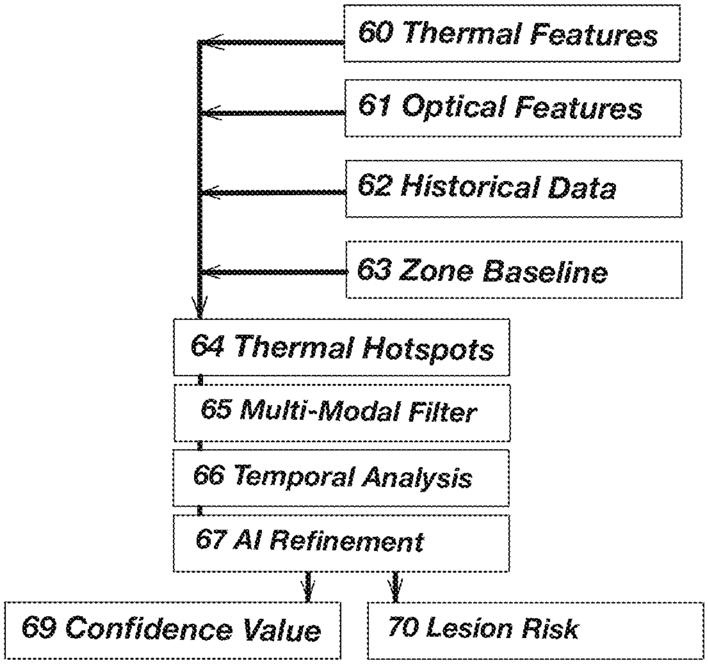
FIG. 5 is a schematic diagram illustrating an example machine-learning architecture for processing thermal, visible-light, and/or temporal features to generate one or more outputs, including a lesion risk score and an associated confidence value.

As illustrated in FIG. 4 Steps 45-48 and FIG. 5, the system applies a staged decision pipeline that converts the registered multi-modal dataset into predictive outputs. In certain embodiments, the pipeline prioritizes thermal anomalies as an early indicator of sub-surface inflammation and uses RGB features primarily for rejecting false positives and characterizing inflammation stage.

In one embodiment, the pipeline comprises:

Step 45: Thermal anomaly detection (candidate hotspot generation).

Step 46: Multi-modal filtering using aligned RGB data (artifact rejection and pre-lesion signature checking).

Step 47: Temporal persistence verification using longitudinal scans.

Step 48: Machine-learning scoring to generate a lesion risk score and a confidence value.

In certain embodiments, calibration-quality indicators derived from the SD (including the RGB-read thermochromic indicator state and/or associated consistency checks) are provided as additional inputs to later scoring so that low-quality scans yield lower confidence rather than incorrect high-risk alerts.

Anatomical Zone Segmentation

Following registration, the system performs anatomical zone segmentation (e.g., FIG. 4 Step 44) to normalize expected thermal variability across different facial regions. In certain embodiments, the system detects facial landmarks in the RGB image and partitions the face into zones (e.g., forehead, left cheek, right cheek, chin) and generates exclusion masks for non-skin regions.

In one embodiment, each pixel (x, y) in the registered dataset is assigned a zone label Z(x, y), and per-zone summary statistics are computed, including zone mean temperature, zone thermal variance, and zone redness baselines. Zone labeling enables adaptive thresholds and reduces false positives that arise when using a single global threshold for anatomically diverse regions.

Anatomical Placements and Region of Interest Adaptation

While some embodiments describes facial analysis, in certain embodiments the system is configured to analyze non-facial skin regions, such as the dorsal hands, wrists, or other body sites subject to inflammatory or pigmentary conditions.

In one embodiment configured for hand skin analysis, the segmentation module partitions the hand image into distinct anatomical zones including: (i) the dorsal hand surface (subdivided into metacarpal regions), (ii) the wrist joint region, (iii) the metacarpophalangeal (MCP) joints (specifically MCP 2 through 5), and (iv) the proximal interphalangeal (PIP) joints.

For pigmentation tracking, the system identifies discrete pigmented lesions (e.g., solar lentigines) on the dorsal hand surface and tracks their specific melanin index relative to the melanin color sample 24 over time.

Thermal Anomaly Detection and Local Contrast Analysis (e.g., FIG. 4, Step 45) In the first detection stage, the system identifies candidate regions of interest (ROIs) from the calibrated temperature map using local contrast rather than absolute temperature alone. In one embodiment, for each pixel (x, y) within a zone Z, the system computes a local temperature contrast $\Delta T(x, y)=T(x, y)-\overline{T}_{nbr}(x, y)$, where $\overline{T}_{nbr}(x, y)$ is a neighborhood mean computed over a predetermined radius.

In certain embodiments, the predetermined radius corresponds to a physical neighborhood on the subject's skin of about 5 mm, such that local hotspot detection is performed relative to nearby surrounding tissue rather than a global facial baseline." "The processor converts the physical neighborhood size to a pixel radius using a mm-per-pixel estimate derived from thermal optics and/or an estimated working distance, such that at close-range facial imaging distances (e.g., about 15-25 cm) each thermal pixel may represent about 0.5-1.0 mm on the skin and a 5 mm radius corresponds to approximately 5-10 pixels." "In certain embodiments, $T_{nbr}(x, y)$ is computed as a robust statistic (mean or median) of valid skin pixels within the radius, optionally excluding non-skin pixels using a skin mask generated during zone segmentation." "Prior to computing $\Delta T(x, y)$, the system may reduce sensor noise by applying mild spatial filtering (e.g., 3×3 or 5×5 smoothing) and/or short-burst averaging across a plurality of thermal frames." "After thresholding, the system may apply non-maximum suppression within the neighborhood radius to retain only the strongest 1-3 hotspot centers per neighborhood and reduce redundant candidate pixels arising from a single warm region.

A candidate hotspot mask is generated when $\Delta T(x, y)$ exceeds a threshold (e.g., about 0.3° C.), optionally followed by connected-component grouping to form ROIs. In certain embodiments, the threshold is adaptive per zone such that naturally warmer regions (e.g., T-zone/forehead and nose region) use a higher threshold than cheeks, thereby improving specificity. In certain embodiments, the adaptive threshold is additionally adjusted using the subject's own historical baseline for the same zone from prior scans to reduce sensitivity to day-to-day physiological fluctuations.

Multi-Modal Filtering

In the second stage, each candidate ROI is cross-referenced against aligned RGB features to reject artifacts that mimic inflammation in thermal images. In certain embodiments, the system rejects candidates overlapping:

- Hair/eyebrows or facial hair regions detected in RGB, which can trap heat and create apparent hotspots.
- Non-skin regions and high-reflectance regions (e.g., eyeglasses glare), which can degrade both thermal and RGB reliability.
- Contact artifacts (e.g., hand-to-face contact) detected by RGB segmentation, which can cause localized heating unrelated to lesion formation.

In certain embodiments, the system evaluates whether a thermal candidate has a corresponding strong visible redness signature and, if present, re-labels the candidate as "already-visible inflammation" rather than a pre-lesion candidate, depending on the desired prediction window behavior.

UV Fluorescence Porphyrin Features

In certain embodiments, the system is configured to perform ultraviolet-excited fluorescence imaging to detect bacterial-associated porphyrins on skin, thereby providing an additional biomarker associated with acne activity and follicular bacterial colonization. In such embodiments, the illumination module described above includes at least one ultraviolet (UV) source configured to emit in the UVA range (for example, approximately 365 nm), and the RGB camera (16) captures one or more corresponding fluorescence frames while the UV source is active.

In certain embodiments, acne-associated fluorescence is observed as orange-red fluorescence in pilosebaceous follicles, attributable to porphyrins associated with Cutibacterium (*Propionibacterium*) *acnes*. In certain embodiments, the system uses optical filtering, including at least one of a long-pass filter over the RGB camera lens and/or a band-pass emission filter, to attenuate reflected UV and preferentially capture visible fluorescence emission in an orange-red spectral region (e.g., around 620-650 nm).

In certain embodiments, the processor (15) computes a per-pixel or per-follicle porphyrin fluorescence index from the UV-illuminated frame and generates a fluorescence map representing a spatial distribution of fluorescent follicular spots. In one non-limiting example, the porphyrin fluorescence index PF(x,y) is computed using a channel ratio, for example PF(x,y)=R_UV(x,y)/(G_UV(x,y)+ε), and/or a red-channel excess metric, for example PF(x,y)=R_UV(x,y)−G_UV(x,y), and the resulting fluorescence map is thresholded and clustered to identify fluorescent follicular candidates.

In certain embodiments, the fluorescence map is stored as an additional modality aligned to the visible-light coordinate frame and is optionally fused with (i) a thermal elevation map and/or (ii) oxyhemoglobin and deoxyhemoglobin maps to improve specificity of pre-lesion prediction and to reduce false positives due to non-pathologic vasodilation. In certain embodiments, the system further uses polarization optics (e.g., a cross-polarized configuration during fluorescence acquisition) to suppress surface glare and improve visibility of fluorescent follicular spots.

Integration of UV Fluorescence with Multi-Spectral Imaging

In certain embodiments, the system integrates UV-excited fluorescence imaging with a multi-spectral reflectance imaging sequence to generate a combined dataset that includes (i) chromophore maps (e.g., melanin, HbO2, Hb, and/or SO2) from reflectance and (ii) a porphyrin fluorescence map indicative of acne-associated bacterial activity. In such embodiments, UV illumination (e.g., UVA centered near 365 nm) is used to excite fluorescence, and an emission barrier filter is used to attenuate reflected UV while transmitting longer-wavelength fluorescence emission to the RGB camera (16).

(a) Acquisition ordering and frame types. In certain embodiments, the processor (15) performs a wavelength-sequenced capture that includes at least one UV fluorescence frame and a plurality of visible/NIR reflectance frames (e.g., blue, green, red, and optionally NIR) captured under narrow-band illumination as described above. In certain embodiments, the UV fluorescence frame is acquired with the reflectance illuminators off and with the UV source on, while the reflectance frames are acquired with the UV source off to reduce cross-talk between modalities.

(b) Optical filtering and polarization (optional). In certain embodiments, the RGB camera (16) includes an emission filter selected to pass fluorescence emission and reject reflected UV, for example a long-pass barrier filter having a cut-on above the UV excitation band. In certain embodiments, polarization filters are used, including cross-polarized illumination/detection, to reduce glare and improve visibility of follicular fluorescence.

(c) Fluorescence preprocessing and background removal. In certain embodiments, the processor (15) computes a fluorescence image F(x,y) from the UV frame by subtracting a background term (e.g., a dark frame, an ambient frame, and/or a low-pass estimate) to reduce contributions from sensor offset and non-fluorescent reflectance leakage. In certain embodiments, the processor (15) computes a porphyrin fluorescence index PF(x,y) from the UV frame using one or more channel-based metrics (e.g., a red-channel-dominant fluorescence ratio and/or a red-excess measure) to emphasize orange-red follicular fluorescence patterns.

(d) Spatial alignment to reflectance/chromophore maps. In certain embodiments, the processor (15) registers the UV fluorescence frame to the reflectance image coordinate system using the same facial-landmark registration pipeline used for the multi-spectral sequence, thereby producing pixel-aligned maps PF(x,y), M(x,y), O(x,y), and D(x,y). In certain embodiments, the processor (15) rejects frames and/ or ROIs when registration confidence is below a threshold (e.g., due to motion) to avoid false localization of follicular fluorescence.

(e) Fusion into multi-modal features and outputs. In certain embodiments, the processor (15) forms an augmented feature tensor per pixel and/or per ROI that includes at least calibrated thermal features, chromophore features (melanin, HbO2, Hb, total hemoglobin, and/or SO2), and porphyrin fluorescence features. In certain embodiments, the system outputs a combined acne-relevant follicular activity map by combining porphyrin fluorescence with vascular and thermal markers, such that a region exhibiting elevated thermal signal together with elevated oxyhemoglobin and localized porphyrin fluorescence is assigned a higher pre-lesion risk score than a region exhibiting thermal signal alone.

(f) Longitudinal tracking (optional). In certain embodiments, the processor (15) stores PF(x,y) and ROI-aggregated fluorescence statistics across scan sessions to quantify changes in follicular fluorescence over time and to evaluate response to interventions, while concurrently tracking erythema and pigmentation trends using chromophore maps as described above for longitudinal analysis.

The Pre-Lesion Signature

After multi-modal filtering, the system identifies a "pre-lesion signature" intended to represent early dermal inflammation before strong surface-level erythema appears. In one embodiment, a pre-lesion candidate satisfies both: (i) elevated local thermal contrast above a threshold and (ii) low or below-threshold erythema/redness proxy in the corresponding RGB region. This combination is used to identify a predictive window in which intervention may be recommended before a lesion becomes clearly visible.

Temporal Persistence and Longitudinal Tracking (e.g., FIG. 4, Step 47)

A single scan may capture transient events (e.g., flushing), so the system applies temporal persistence rules using historical user data. In one embodiment, the system tracks candidate ROI locations across successive scan sessions and determines whether the candidate persists for at least two consecutive scans separated by a predetermined interval (e.g., approximately 24 hours).

In certain embodiments, the system further requires that ΔT for the ROI is stable or increasing over time, and rejects candidates whose contrast rapidly decreases, indicating a transient event rather than a developing lesion. Temporal tracking may be performed in zone coordinates and/or via registration-stabilized pixel coordinates to maintain consistent localization despite pose variation.

AI Refinement and Scoring—Model Integration (e.g., FIG. 4, Step 48)

In the final scoring stage, the system generates a lesion probability and an associated confidence score for each candidate ROI and/or for each anatomical zone. In certain embodiments, the scoring engine comprises a machine learning model (e.g., a CNN classifier, a gradient-boosted classifier, or a recurrent model using longitudinal features) that consumes an engineered feature vector derived from thermal, RGB, and temporal data.

In one embodiment, the feature vector includes:

Thermal features: max ΔT, ROI area, thermal gradient statistics, and per-zone baselines.

Optical features: erythema proxy, texture features, and skin-pixel validity metrics.

Temporal features: persistence duration and trend metrics.

Calibration/quality features: SD-derived quality indicators (including agreement checks enabled by the thermochromic indicator readout) to down-weight unreliable scans.

The model outputs a Lesion Risk Score and a Confidence Value so that the user interface can distinguish "high risk with high confidence" from "uncertain scan requiring re-acquisition."

Output Generation (e.g., FIG. 4, Steps 49-50)

Referring to FIG. 4, after output generation (Step 49), the host device stores at least one of: (i) per-zone and/or per-candidate Lesion Risk Score and Confidence Value, (ii) coordinates and geometry of candidate ROIs, and (iii) extracted thermal/optical/temporal features used to generate the score. In certain embodiments, the output includes a visual overlay on the RGB image indicating the predicted location(s) with a color-coded risk level and a text instruction associated with the zone.

In certain embodiments, the system prompts the user for follow-up feedback (e.g., whether a predicted lesion became visible later), and stores the feedback for personalization and improvement of the predictive model over time. In certain embodiments, risk thresholds (e.g., high risk, moderate risk) are used to trigger different recommendations, such as preventative spot treatment guidance or monitoring guidance.

Table 1 summarizes the FIG. 4 end-to-end workflow from scan initiation through calibration, registration, candidate detection, and risk-score output/storage. The flow reflects the SD-18 embodiment that includes dual-emissivity regions (21/22) and an RGB-readable thermochromic liquid-crystal temperature indicator (23) used to anchor absolute $T_{skin}$ and simplify/strengthen in-field radiometric calibration.

TABLE 1

FIG. 4 PROCESS FLOW SUMMARY

| Step | Phase | Description | Key output/ input |
|---|---|---|---|
| 40 | Initialization | Initiate a scan session, prompt user to wear/position SD-18, and confirm SD18 visibility and working distance readiness. | Session start/ readiness flags. |
| 41 | Image acquisition | Capture synchronized thermal frames (burst) and RGB frames covering the skin and SD-18. In certain embodiments, Step 41 further comprises performing wavelength-sequenced acquisition using a multi-spectral active illumination module by sequentially activating a plurality of narrow-band emitters (e.g., blue, green, red, and optionally UV and/or NIR) and capturing one or more corresponding RGB frames per | Raw thermal frames + raw RGB frames. |

TABLE 1-continued

FIG. 4 PROCESS FLOW SUMMARY

| Step | Phase | Description | Key output/ input |
|---|---|---|---|
| | | wavelength, thereby forming a multi-spectral visible-light image set. In such embodiments, each captured visible-light frame is stored with metadata identifying wavelength band, exposure settings, and timestamp, and the multi-spectral set is optionally motion-compensated (e.g., by applying facial-landmark registration parameters derived from a reference frame) to produce a spatially aligned multi-spectral stack suitable for chromophore mapping and longitudinal analysis. | |
| 42 | Radiometric calibration | Preprocess thermal data (e.g., NUC/denoise), detect SD regions 21/22, read absolute T-skin from thermochromic indicator 23 in RGB, and solve in-field gain G' and offset O to generate a calibrated facial temperature map. | Calibrated absolute temperature map + calibration quality metrics. |
| 43 | Registration | Detect SD-18 fiducials in both modalities and compute a geometric transform (e.g., homography) to warp the calibrated thermal map into RGB coordinates. | Registered multi-modal dataset (thermal-in-RGB coordinates). |
| 44 | Zone segmentation | Perform facial landmark detection and partition the skin into anatomical ROIs; generate exclusion masks for non-skin regions (eyes/lips/nostrils/hair). | Zone labels Z(x,y) + skin-validity mask. |
| 45 | Thermal anomaly detection | Compute local thermal contrast ΔT and apply adaptive per-zone thresholds to identify candidate thermal hotspots. | Candidate hotspot ROIs (thermal). |
| 46 | Multi-modal filtering | Reject artifacts using aligned RGB (hair/contact/non-skin) and apply the pre-lesion signature rule (high ΔT with low erythema proxy). | Filtered candidate ROIs (pre-lesion candidates). |
| 47 | Temporal analysis | Verify persistence and trend across prior sessions for the same zone/location to reject transient flushing and confirm developing patterns. | Confirmed pre-lesion candidates + temporal features. |
| 48 | AI refinement | Generate a risk probability and confidence value using a predictive model fed by thermal/optical/temporal features and quality signals. | Lesion Risk Score + Confidence Value. |
| 49 | Output generation | Present per-zone/per-ROI risk results and optionally render an overlay on the RGB image with actionable guidance thresholds. | User-facing results (risk, confidence, location). |
| 50 | Session finalization | Store session outputs and features for longitudinal tracking and optionally collect user feedback for personalization. | Stored history (risk trends, candidate logs, feedback). |

Relationship Between FIG. 4 and FIG. 5

FIG. 4 illustrates an end-to-end scan-session method including (i) acquisition of synchronized thermal and RGB data, (ii) in-field radiometric calibration using the wearable SD-18, (iii) thermal-to-RGB registration, (iv) anatomical zone segmentation, and (v) detection, scoring, and storage of predicted pre-lesion events. FIG. 5 illustrates an implementation-level block diagram of the predictive inference portion of FIG. 4, in which thermal, optical, temporal, and context features are processed through staged modules to produce a Lesion Risk Score 70 and a Confidence Value 69.

In one embodiment, the outputs of FIG. 4 Steps 42-44 provide the principal inputs to FIG. 5, including Thermal Features 60 derived from the calibrated temperature map and Optical Features 61 derived from the registered RGB image. In certain embodiments, the SD-18 includes a thermochromic liquid-crystal temperature indicator (region 23) whose RGB readout provides an absolute local $T_{skin}$ used during Step 42 to reduce calibration uncertainty, and a calibration quality metric derived therefrom is optionally included as part of Historical User Data 62 and/or Zone Baseline/Context 63 to modulate later confidence scoring. The staged blocks in FIG. 5 correspond directly to later steps of FIG. 4, namely Thermal Hotspot Detection 64↔Step 45, Multi-Modal Filtering 65↔Step 46, Temporal Analysis 66↔Step 47, and AI Refinement/Classifier 67↔Step 48, with the resulting outputs provided in Step 49 and stored in Step 50.

Neural Network Architecture for Risk Prediction

This section describes a machine-learning model configured to implement the AI refinement stage of the method (e.g., FIG. 4 Step 48 and FIG. 5 block 67) by predicting, for one or more facial zones, a probability that a visible inflammatory lesion will emerge within a future time window and by generating an associated confidence value. In certain embodiments, the model operates on engineered per-zone features rather than raw images, wherein the features are constructed from the registered multi-modal dataset (thermal+RGB) and optionally include temporal derivatives computed from historical scans.

As shown conceptually in FIG. 5, the model receives a set of inputs including Thermal Features 60, Optical Features 61, Historical User Data 62, and Zone Baseline/Context 63, and produces outputs Lesion Risk Score 70 and Confidence Value 69. In certain embodiments, the input features further include calibration/quality indicators derived from the SD-based calibration stage, including at least one metric related to the thermochromic indicator 23 readout used to anchor absolute $T_{skin}$, such that low-quality calibration conditions reduce confidence without necessarily suppressing true-positive risk patterns.

In one embodiment, the model is a spatio-temporal architecture that encodes per-day per-zone feature vectors and applies a temporal sequence model (e.g., an LSTM or equivalent recurrent unit) to learn longitudinal patterns that precede lesion emergence rather than merely classifying current visible state. In certain embodiments, the network includes a dual-head output in which a first head outputs risk and a second head outputs confidence, enabling the user interface to distinguish high-risk/high-certainty outputs from outputs requiring re-acquisition or additional follow-up scans. In certain embodiments, the trained model is deployed for on-device inference to support offline operation and privacy-preserving processing on consumer mobile devices.

FIG. 5 Element Summary

Table 2 provides an element-by-element legend for FIG. 5, which depicts the predictive scoring pipeline that operates on registered multi-modal features to output a Lesion Risk Score and an associated Confidence Value. In certain embodiments, FIG. 5 operates on features produced by the FIG. 4 workflow (calibration, registration, and zone segmentation), and optionally incorporates scan-quality signals enabled by the SD-18, including the RGB-readable thermochromic temperature indicator (region 23) used to anchor absolute T-skin.

TABLE 2

| No. | Element Name | Brief Description |
|---|---|---|
| 60 | Thermal Features | Per-zone thermal feature vector derived from the calibrated temperature map, including at least one of zone mean temperature, local contrast ΔT statistics, hotspot count, hotspot area, and thermal gradient metrics. |
| 61 | Optical Features | Per-zone RGB-derived feature vector including at least one of erythema proxy metrics, texture features, and skin-mask validity indicators produced after thermal-to-RGB registration. |
| 62 | Historical User Data | Longitudinal record of prior scan features and/or prior risk outputs for the same subject, used to compute persistence and trends and to personalize zone baselines. |
| 63 | Zone Baseline/ Context | Zone-specific baseline values and adaptive thresholds (e.g., forehead vs. cheek), optionally including context such as time-of-day and scan-quality signals that affect interpretation of ΔT and redness proxies. |
| 64 | Thermal Hotspot Detection | First-stage processing operation, executed by the processor (15), that identifies candidate ROIs by computing local thermal contrast and applying adaptive thresholds to generate hotspot candidates. |
| 65 | Multi-Modal Filtering | Second-stage processing operation, executed by the processor (15), that rejects candidates using aligned RGB data (hair/non-skin/contact artifacts) and applies the pre-lesion signature check (high thermal contrast with low erythema proxy). |
| 66 | Temporal Analysis | Processing operation, executed by the processor (15), that evaluates persistence, growth, and/or stability of candidates across multiple scan sessions using historical data, rejecting transient events. |
| 67 | AI Refinement/ Classifier | Predictive model block that consumes the filtered and temporally-qualified features to output risk and confidence, and may include a temporal sequence component (e.g., LSTM) and dual output heads. |
| 69 | Confidence Value | Scalar confidence score output by the model indicating reliability of the risk prediction for a zone and/or ROI, optionally influenced by data quality and calibration consistency. |
| 70 | Lesion Risk Score | Scalar risk value (e.g., scaled 0-100) representing predicted likelihood that a visible lesion will emerge within a future time window (e.g., 24-48 hours). |

Example Scan Session

In one non-limiting example of use, a subject enters a room, activates a host device (15), and selects a facial region of interest (ROI) on a user interface displayed on screen (11). The subject positions the standard device SD-18 adjacent to the ROI within the common field of view of the thermal infrared imaging module (12) and the visible-light camera, and then presses a "ready" control. In response, processor (15) activates the illumination module (17) and acquires synchronized thermal and visible-light images. A control unit (207) executes a PID loop that adjusts the temperatures of thermal reference regions (204, 205, 206) so that their radiometric values bracket or approximate the radiometric values measured in the facial ROI, based on real-time data from thermal camera (12) and temperature sensors (203) coupled to the reference regions. Using the known emissivity and measured temperatures of regions (204, 205, 206), the processor computes calibration parameters for the thermal infrared imaging module and generates a calibrated facial temperature map. The calibrated temperature map is then registered to the visible-light image using anatomical landmarks and/or SD-18 features, and the resulting multi-modal data are stored and incorporated into longitudinal analysis, including computation of lesion risk scores, erythema and pigmentation trends, and generation of a cosmetic-purpose report for the subject.

AI Prediction Overview (e.g., FIGS. 4-5)

In certain embodiments, FIG. 4 Steps 45-50 are implemented by the predictive pipeline shown in FIG. 5, which transforms calibrated and registered thermal-optical measurements into (i) a Lesion Risk Score and (ii) an optional Confidence Value. FIG. 5 receives inputs derived from the prior stages of FIG. 4, including radiometrically calibrated facial temperature values and aligned RGB image data, and outputs a per-zone and/or per-region prediction indicating likelihood of an inflammatory lesion becoming visibly apparent within a future time window.

In certain embodiments, the model operates on per-zone features rather than raw pixel imagery to reduce computation, simplify implementation on consumer devices, and improve robustness to lighting, pose, and sensor drift. The inputs and intermediate blocks may correspond to FIG. 5 elements 60-67 and the outputs may correspond to FIG. 5 elements 69-70, as previously described.

Feature Construction Inputs (e.g., FIG. 5, Elements 60-63)

In certain embodiments, after FIG. 4 Steps 42-44 (calibration, registration, and zone labeling), the system constructs, for each anatomical zone Z (or for each candidate ROI within a zone), a compact per-zone feature vector for input to the predictive pipeline of FIG. 5, including Thermal Features (FIG. 5 element 60), Optical Features (FIG. 5 element 61), Historical User Data (FIG. 5 element 62), and Zone Baseline/Context (FIG. 5 element 63). In such embodiments, the feature vector is computed by aggregating pixel-level channels from the fused representation F(x,y) (e.g., temperature, RGB-derived indices, and optional additional modalities) over valid skin pixels of the zone using the skin-validity mask and exclusion masks (eyes, lips, nostrils, hair).

Thermal Features (60) may include at least one of: zone mean temperature, robust baseline temperature (e.g., median), local contrast statistics $\Delta T$ relative to surrounding tissue, hotspot count, hotspot area, hotspot peak $\Delta T$ or peak temperature, and thermal gradient statistics derived from the registered calibrated temperature map. Optical Features (61) may include at least one of: erythema proxy metrics derived from the corrected RGB image (e.g., red-green ratios, normalized red reflectance, HSV-based redness measures), texture or high-frequency measures, and validity indicators (e.g., percent masked pixels) used to suppress false positives caused by glare, cosmetics, hair occlusion, and non-skin regions.

In certain embodiments, when multi-spectral reflectance processing is enabled, Optical Features (61) further include chromophore-derived summary statistics computed from one or more registered chromophore maps, including at least one of a melanin-related channel M(x,y), an oxyhemoglobin channel O(x,y), a deoxyhemoglobin channel D(x,y), total hemoglobin H_tot(x,y), and/or oxygen saturation S_O2 (x,y), aggregated per zone as one or more of mean, median, percentile values, spatial variance, and/or localized extrema within a hotspot neighborhood. In certain embodiments, when UV-excited fluorescence is enabled, Optical Features (61) further include one or more porphyrin fluorescence features derived from a registered porphyrin fluorescence index PF(x,y), including at least one of PF mean within the zone, PF maximum, and/or a follicular-spot count/density computed by thresholding and clustering PF(x,y) within valid skin pixels.

Historical User Data (62) may include stored per-zone feature vectors from prior scan sessions for the same subject and corresponding prior outputs (e.g., prior risk scores), enabling computation of persistence and trend features rather than single-session classification.

Zone Baseline/Context (63) may include zone identity (e.g., forehead vs. cheek), adaptive thresholds and normalization parameters, and scan metadata such as estimated working distance, pose quality, and time-of-day, which affect interpretation of temperature contrast and redness proxies. In certain embodiments, Zone Baseline/Context (63) further includes one or more scan-quality indicators derived from the SD-based calibration and from registration confidence (e.g., SD visibility/segmentation confidence, indicator readout validity, and/or transform residual error), and such indicators are used to down-weight affected channels, request reacquisition, and/or reduce the confidence output without necessarily suppressing a true-positive risk pattern.

Temporal Representation

In certain embodiments, the system stores one or more prior-session per-zone feature vectors for the same user as Historical User Data (FIG. 5 element 62), enabling persistence and trend analysis rather than single-session classification. In such embodiments, a temporal representation is formed by assembling a sequence of feature vectors corresponding to a plurality of scan sessions for a same anatomical zone and/or a same tracked candidate ROI, and the sequence is provided to Temporal Analysis (FIG. 5 element 66) and/or to an AI refinement model that includes a temporal component.

In certain embodiments, Temporal Analysis (FIG. 5 element 66) applies persistence and trend gating to reject transient physiological events (e.g., short-lived flushing), including requiring that a candidate region satisfy a persistence criterion across multiple scans and/or exceed a minimum change criterion over a defined interval. In certain embodiments, the temporal gating is applied before a final classifier or confidence scoring stage to reduce false positives and to improve interpretability of the final risk output.

In certain embodiments, when optional chromophore and/or UV fluorescence channels are enabled, the temporal representation further supports evaluation of longitudinal multi-signal patterns by tracking changes in vascular chromophore features and/or porphyrin fluorescence features in the same registered zone or ROI across scan sessions.

Risk Model and Outputs

In certain embodiments, the prediction stage comprises: (i) Thermal Hotspot Detection (FIG. 5 element 64), (ii) Multi-Modal Filtering (FIG. 5 element 65), (iii) Temporal Analysis (FIG. 5 element 66), and (iv) AI Refinement (FIG. 5 element 67) that produces a final Lesion Risk Score (FIG. 5 element 70) for each zone and/or candidate ROI. The AI Refinement block may comprise at least one of: a multilayer perceptron, a recurrent neural network, a temporal convolutional network, logistic regression, or gradient-boosted decision trees, trained using labeled longitudinal datasets to predict lesion emergence within a defined horizon.

In certain embodiments, the system outputs both (a) the Lesion Risk Score and (b) a Confidence Value (FIG. 5 element 69), where confidence is reduced when scan-quality indicators (e.g., poor registration, low SD visibility, or calibration inconsistency) exceed predefined tolerances. The risk and confidence outputs are then used in FIG. 4 Steps 49-50 to generate an overlay or zone-level display for the user and to store results for longitudinal tracking.

What is claimed is:

1. A skin analysis system, comprising:

a thermal camera configured to capture at least one thermal image of skin of a user, the at least one thermal image comprising thermal image data;

a visible-light camera configured to capture at least one visible-light image of the skin of the user, the at least one visible-light image comprising visible-light image data;

a calibration device comprising a plurality of thermal reference regions and a plurality of visible-light reference features; and at least one processor operably coupled to the thermal camera and the visible-light camera, wherein the thermal camera and the visible-light camera are configured to acquire, during a same data-acquisition event, (A) the at least one thermal image and (B) the at least one visible-light image, while the calibration device is within a field of view of the thermal camera and within a field of view of the visible-light camera, wherein the skin of the user has not been cooled immediately prior to the same data-acquisition event, and wherein the at least one processor is operatively connected to at least one non-transitory, computer readable medium having instructions stored thereon that, when executed by a computing device, cause the computing device to perform operations, the operations comprising:

performing radiometric calibration of the thermal image data using the plurality of thermal reference regions to obtain calibrated thermal image data;

registering at least a portion of the calibrated thermal image data with at least a portion of the visible-light image data using the plurality of visible-light reference features and the plurality of thermal reference regions to associate thermal values and visible-light values with corresponding skin locations;

determining, based on the registered calibrated thermal image data and the registered visible-light image data, one or more candidate skin regions exhibiting localized thermal elevation exceeding a thermal threshold while a corresponding visible-light metric remains below a visible inflammatory threshold, thereby identifying a developing condition prior to clear visibility under normal viewing conditions; and generating, based on the determining the one or more candidate skin regions, an output indicative of a predicted future visible manifestation for the one or more candidate skin regions, wherein the predicted future visible manifestation is of at least one acne-related condition selected from the group consisting of: inflammation, redness, erythema, or pigmentation, within a future time window, wherein the thermal camera is configured to sense radiation in a spectral band of 8-14 micrometers.

2. The system of claim 1, wherein the calibration device is a wearable device configured to be in thermal contact with the skin of the user, and wherein the plurality of visible-light reference features comprises a thermochromic optical indicator configured to provide a visual indication of absolute skin temperature detectable by the visible-light camera, and wherein the plurality of thermal reference regions have different emissivity characteristics detectable by the thermal camera.

3. The system of claim 2, wherein the operations further include deriving an absolute skin temperature value from a color state of the thermochromic optical indicator captured in the visible-light image data and using the absolute skin temperature value to calibrate a radiometric response of the thermal camera.

4. The system of claim 1, wherein the calibration device comprises a melanin reference region having a spectral reflectance profile that mimics an absorption spectrum of human eumelanin, wherein the operations further comprise computing a normalized melanin index for a skin region by:

measuring a first set of color values from the melanin reference region in the visible-light image data;

measuring a second set of color values from the skin region in the visible-light image data; and normalizing the second set of color values against the first set of color values to generate the normalized melanin index, thereby compensating for variations in ambient illumination and sensor response across different scan sessions.

5. The system of claim 1, wherein the corresponding visible-light metric is a visible inflammatory metric, and the visible inflammatory metric being below the visible inflammatory threshold distinguishes a developing sub-clinical condition from an already-visible inflammatory lesion.

6. The system of claim 1, wherein the operations further comprise: computing, for skin pixels in the visible-light image data, at least one erythema metric selected from (i) a red-green index, (ii) a normalized red reflectance, or (iii) a hue-saturation metric in an HSV color space, to form a spatial erythema map; and wherein the output comprises a likelihood, based at least in part on the spatial erythema map, that a visible inflammatory lesion will emerge within the future time window.

7. The system of claim 1, wherein the operations further comprise storing historical data from a plurality of scan sessions.

8. The system of claim 7, wherein the operations further comprise tracking a multi-stage thermal-erythema-pigmentation cascade across the plurality of scan sessions by:

detecting a persistent thermal elevation in a specific skin region in a first set of scan sessions;

detecting an increase in an erythema metric in the specific skin region in a subsequent second set of scan sessions; and generating a pigmentation risk alert predicting post-inflammatory hyperpigmentation for the specific skin region before a normalized melanin index for the specific skin region exceeds a visible hyperpigmentation threshold.

9. The system of claim 7, wherein the operations further comprise evaluating a suitability of a cosmetic product applied to the skin by:

calculating a longitudinal redness trend from the visible-light image data across the plurality of scan sessions during a period of use of the cosmetic product;

detecting whether the longitudinal redness trend exhibits a positive slope exceeding a predetermined irritation threshold; and generating a product intolerance alert when the longitudinal redness trend exceeds the predetermined irritation threshold, thereby indicating the cosmetic product is unsuitable for the user.

10. The system of claim 1, wherein the determining the one or more candidate skin regions comprises detecting that the localized thermal elevation exceeds the thermal threshold in the registered calibrated thermal image data and rejecting at least one false-positive candidate using the corresponding visible-light metric derived from the visible-light image data.

11. The system of claim 10, wherein the rejecting the at least one false-positive candidate comprises:

identifying at least one artifact region in the registered visible-light image data corresponding to a hair region, a high-reflectance glare region, or a hand-contact region;

determining a spatial overlap between the localized thermal elevation and the at least one artifact region; and excluding the localized thermal elevation from being classified as a candidate skin region when the spatial overlap exceeds a predetermined threshold.

12. The system of claim 1, wherein the calibration device is a non-wearable device positioned within the field of view of the thermal camera, and wherein the calibration device comprises a heating element and a temperature controller configured to receive control signals to independently adjust temperatures of the plurality of thermal reference regions.

13. The system of claim 12, wherein the calibration device is positioned within the field of view of the thermal camera during the same data-acquisition event such that the thermal image data includes thermal signals from both the skin of the user and the plurality of thermal reference regions of the calibration device, the plurality of thermal reference regions having independently controllable temperatures, wherein the operations further comprise:

identifying a region of interest (ROI) of the skin in a preliminary thermal image data set before the thermal image data is acquired, and determining a thermal signal value associated with the ROI;

determining a set of target temperatures for the plurality of thermal reference regions such that at least a first target temperature in the set of target temperatures is below the thermal signal value and at least a second target temperature in the set of target temperatures is above the thermal signal value;

transmitting a control signal to the temperature controller of the calibration device to drive the plurality of thermal reference regions to the set of target temperatures; and after the thermal image data has been acquired, calibrating the thermal image data using the plurality of thermal reference regions at the set of target temperatures.

14. The system of claim 1, further comprising a multi-spectral illumination module configured to emit ultraviolet (UV) radiation, wherein the operations further comprise:

acquiring, by the visible-light camera, a fluorescence image of the skin during UV illumination to detect porphyrin signals associated with bacterial activity;

registering the fluorescence image with the thermal image data; and increasing a likelihood that a visible inflammatory lesion will emerge for a candidate skin region of the one or more candidate skin regions when the localized thermal elevation spatially coincides with a detected porphyrin signal, thereby distinguishing bacterial inflammation from non-bacterial thermal anomalies.

15. The system of claim 1, wherein the at least one visible-light image comprises a plurality of visible-light images acquired under different illumination wavelength bands.

16. The system of claim 15, wherein the operations further comprise separating vascular inflammation from pigmentation by:

performing spectral unmixing to the plurality of visible-light images to generate an oxyhemoglobin distribution map and a melanin distribution map; and validating a candidate skin region of the one or more candidate skin regions as an active inflammatory event only when a localized thermal elevation corresponds to a localized increase in the oxyhemoglobin distribution map, independent of the melanin distribution map.

17. The system of claim 15, wherein the operations further comprise computing a tissue oxygen saturation metric for a candidate skin region of the one or more candidate skin regions by comparing an oxyhemoglobin signal and a deoxyhemoglobin signal derived from the plurality of visible-light images acquired under different illumination wavelength bands, and wherein the output comprises an indication of whether the developing condition represents an acute inflammatory phase characterized by elevated oxygen saturation.

18. The system of claim 1, wherein the thermal camera comprises an uncooled microbolometer array having a noise-equivalent temperature difference (NETD) of less than 50 millikelvin (mK).

19. The system of claim 1, wherein the visible-light camera has a resolution of at least 8 megapixels.

20. The system of claim 1, wherein the thermal threshold is a local thermal elevation threshold of at least 0.3° C., wherein the local thermal elevation is computed as a difference between:

(a) a temperature value of a candidate pixel or candidate region in the calibrated thermal image data; and (b) a reference temperature value selected from at least one of:

(i) a mean temperature of a surrounding neighborhood of the candidate pixel or candidate region;

(ii) a zone baseline temperature computed for an anatomical zone containing the candidate pixel or candidate region; or (iii) a subject-specific historical baseline temperature for a corresponding skin location derived from one or more prior data-acquisition events.

21. The system of claim 1, wherein the future time window is a prediction horizon of approximately 24 to 48 hours, wherein the output indicative of the predicted future visible manifestation comprises:

(a) a likelihood that a visible inflammatory lesion will emerge within the prediction horizon; and (b) an indicator of reliability of the likelihood that the visible inflammatory lesion will emerge within the predicted horizon, wherein the indicator of reliability is reduced when at least one scan-quality parameter exceeds a predetermined tolerance.

22. A method for cosmetic skin analysis, comprising:

positioning a calibration device comprising a plurality of thermal reference features and a plurality of visible-light reference features within a field of view of a thermal camera and within a field of view of a visible-light camera;

capturing, during a same data-acquisition event while the calibration device remains within the field of view of the thermal camera and within the field of view of the visible-light camera, (A) thermal image data of skin of a user using the thermal camera and (B) visible-light image data of the skin using the visible-light camera, wherein the skin of the user has not been cooled immediately prior to the same data-acquisition event;

performing radiometric calibration of the thermal image data using the at least one thermal reference feature to obtain calibrated thermal image data;

registering at least a portion of the calibrated thermal image data with at least a portion of the visible-light image data using the plurality of visible-light reference features and the plurality of thermal reference features to associate thermal values and visible-light values with corresponding skin locations;

determining, based on the registered calibrated thermal image data and the registered visible-light image data, one or more candidate skin regions exhibiting a localized thermal elevation exceeding a thermal threshold while a corresponding visible-light metric remains below a visible inflammatory threshold, thereby identifying a developing condition prior to clear visibility under normal viewing conditions; and generating, based on the determining the one or more candidate skin regions, an output indicative of a predicted future visible manifestation for the one or more candidate skin regions, wherein the predicted future visible manifestation is of at least one acne-related condition selected from the group consisting of: inflammation, redness, erythema, or pigmentation, within a future time window, wherein the thermal camera is configured to sense radiation in a spectral band of 8-14 micrometers.

23. The method of claim 22, further comprising:

positioning the calibration device in thermal contact with the skin within the field of view of the thermal camera and the field of view of the visible-light camera, wherein the calibration device comprises a thermochromic optical indicator; and calibrating a radiometric response of the thermal camera by deriving an absolute skin temperature value from a color state of the thermochromic optical indicator captured in the visible-light image data and using the absolute skin temperature value to correct the thermal image data.

24. The method of claim 22, further comprising:

positioning the calibration device within the field of view of the thermal camera such that the calibration device is thermally isolated from the skin, wherein the plurality of thermal reference regions have independently controllable temperatures;

identifying a region of interest (ROI) of the skin in a preliminary thermal image data set before the thermal image data is acquired;

determining a thermal signal value of the ROI;

driving the plurality of thermal reference regions to a set of target temperatures such that at least a first target temperature in the set of target temperatures is below the thermal signal value and at least a second target temperature in the set of target temperatures is above the thermal signal value; and calibrating the thermal camera using the plurality of thermal reference regions at the set of target temperatures.

25. The method of claim 22, wherein the thermal threshold is a local thermal elevation threshold of at least 0.3° C., wherein the local thermal elevation is computed as a difference between:

(a) a temperature value of a candidate pixel or candidate region in the calibrated thermal image data; and (b) a reference temperature value selected from at least one of:

(i) a mean temperature of a surrounding neighborhood of the candidate pixel or candidate region;

(ii) a zone baseline temperature computed for an anatomical zone containing the candidate pixel or candidate region; or (iii) a subject-specific historical baseline temperature for a corresponding skin location derived from one or more prior data-acquisition events.

26. The method of claim 22, wherein the future time window is a prediction horizon of approximately 24 to 48 hours, wherein he output indicative of the predicted future visible manifestation comprises:

a likelihood that a visible inflammatory lesion will emerge within the prediction horizon; and an indicator of reliability of the likelihood that the visible inflammatory lesion will emerge within the predicted horizon, wherein the indicator of reliability is reduced when at least one scan-quality parameter exceeds a predetermined tolerance.

* * * * *